(12) United States Patent
Révész

(10) Patent No.: US 6,919,336 B2
(45) Date of Patent: Jul. 19, 2005

(54) HALLOGENATED AMINOBENZOPHENONES AND AMINOBENZOYLPYRIDINES AS INHIBITORS OF IL-1 AND TNF

(75) Inventor: Lászlo Révész, Therwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/471,568

(22) PCT Filed: Mar. 22, 2002

(86) PCT No.: PCT/EP02/03267

§ 371 (c)(1),
(2), (4) Date: Sep. 11, 2003

(87) PCT Pub. No.: WO02/076447

PCT Pub. Date: Oct. 3, 2002

(65) Prior Publication Data

US 2004/0097731 A1 May 20, 2004

(30) Foreign Application Priority Data

Mar. 23, 2001 (GB) ............................................. 0107368

(51) Int. Cl.[7] ................... C07D 213/02; C07D 401/02; A61K 31/44

(52) U.S. Cl. ............... 514/231.5; 514/253.01; 514/332; 514/339; 514/352; 514/646; 546/255; 546/273.4; 546/310; 544/106; 544/124; 544/333; 544/359; 564/319

(58) Field of Search ................................. 514/352, 646, 514/231.5, 253.01, 332, 339; 564/319; 546/310, 255, 273.4; 544/106, 124, 333, 359

(56) References Cited

FOREIGN PATENT DOCUMENTS

WO   WO 9832730 A   *   7/1998

OTHER PUBLICATIONS

Bhavsar et al, Man–Made Textiles in India, vol. 30, No 6, pp. 275–276, 281, 1987.*

* cited by examiner

Primary Examiner—Zinna Northington Davis
(74) Attorney, Agent, or Firm—E. Jay Wilusz, Jr.

(57) ABSTRACT

Compounds of formula I and pharmaceutically-acceptable and -cleavable esters thereof and acid addition salts thereof wherein the symbols are as defined are MAP kinase inhibitors, useful pharmaceutically for treating TNFα and IL-1 mediated diseases such as rheumatoid arthritis and diseases of bone metabolism, e.g. osteoporosis.

9 Claims, No Drawings

HALLOGENATED AMINOBENZOPHENONES AND AMINOBENZOYLPYRIDINES AS INHIBITORS OF IL-1 AND TNF

This invention relates to benzoyl compounds, in particular to benzophenones and benzoylpyridines and to their use for treating TNFα and IL-1 mediated diseases such as rheumatoid arthritis and diseases of bone metabolism, e.g. osteoporosis.

Accordingly the present invention provides a compound of formula I

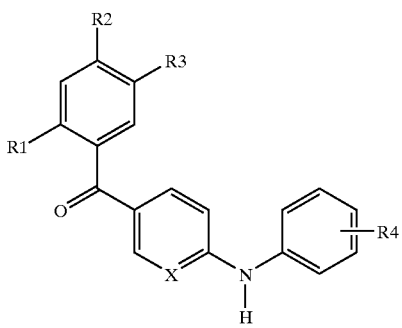

Wherein
X is N or CH;
R1 is H, halogen, or optionally substituted (lower alkoxy, lower alkyl or halo-substituted lower alkyl);
R2 is H, or optionally substituted (heterocyclyl, lower alkyl lower alkene, lower alkyne or lower alkoxy);
R3 is H, or optionally substituted (heterocyclyl, lower alkyl lower alkene, lower alkyne or lower alkoxy); or
R2 and R3 are linked together to form an optionally substituted 4- to 6-membered heterocyclic ring containing one or more hetero atoms selected from O, S, N or NR, where R is H or lower alkyl, and
R4 represents one, two or three independent halogen substituents,
or a pharmaceutically-acceptable and -cleavable ester or acid addition salt thereof.

Above and elsewhere in the present description the following terms have the following meanings.

Halo or halogen denote I, Br, Cl or F.

The term "lower" referred to above and hereinafter in connection with organic radicals or compounds respectively defines such as branched or unbranched with up to and including 7, preferably up to and including 4 and advantageously one or two carbon atoms.

A lower alkyl group is branched or unbranched and contains 1 to 7 carbon atoms, preferably 1–4 carbon atoms. Lower alkyl represents for example methyl, ethyl, propyl, butyl, isopropyl or isobutyl.

Halo-substituted lower alkyl is $C_1$–$C_7$lower alkyl substituted by up to 6 halo atoms.

A lower alkoxy group is branched or unbranched and contains 1 to 7 carbon atoms, preferably 1–4 carbon atoms. Lower alkoxy represents for example methoxy, ethoxy, propoxy, butoxy, isopropoxy, isobutoxy or tertiary butoxy.

A lower alkene or alkenyl group is branched or unbranched and contains 2 to 7 carbon atoms, preferably 1–4 carbon atoms and contains at least one carbon-carbon double bond. Lower alkene or lower alkenyl represents for example vinyl, propenyl, butenyl, isopropenyl or isobutenyl.

A lower alkyne or alkynyl group is branched or unbranched and contains 2 to 7 carbon atoms, preferably 1–4 carbon atoms and contains at least one carbon-carbon triple bond. Lower alkyne or alkynyl represents for example ethynyl, propynyl, butynyl, isopropynyl or isobutynyl.

Heterocyclyl may be aromatic, i.e. as $C_{3-18}$heteroaryl, partially unsaturated comprising from 3 to 18 ring members, or saturated, i.e. as $C_{3-18}$heterocycloalkyl, and comprises at least 3 ring atoms, at least one of which is a hetero atom, e.g. O, S, N, or NR, where R is H or lower alkyl.

R1, R2 and R3 may be further substituted by one or more, e.g. up to six, substituents independently selected from halo, OH, CN, lower alkyl, lower alkoxy, heterocyclyl or NR5R6 where R5 and R6 are independently H or lower alkyl. The lower alkyl, lower alkoxy, heterocyclyl or NR5R6 substituents on R1, R2 and R3 may be further substituted by one or more, e.g. each by up to six, normally up to three, e.g. 1 or 2, substituents independently selected from halo, OH, CN, lower alkyl, lower alkoxy, heterocyclyl or NR5R6 where R5 and R6 are as defined above.

R1 is preferably halo, $C_1$–$C_4$ lower alkyl, $C_1$–$C_4$lower alkoxy or halo-substituted $C_1$–$C_4$ lower alkyl. Most preferably R1 is Cl, F, methoxy, methyl or $CF_3$.

R2 and R3 are preferably, independently of one another, H or optionally substituted ($C_1$–$C_7$alkenyl, $C_1$–$C_7$alkynyl, $C_5$–$C_7$N-heterocyclyl $C_1$–$C_4$lower alkoxy, $C_5$–$C_7$N-heterocyclyl) wherein the $C_5$–$C_7$N-heterocyclyl optionally contains a further hetero atom, e.g. N or O, and the optional substitution comprises 1 or 2 substituents, separately selected from $C_{1-4}$alkyl, halogen, hydroxy, $C_{1-4}$alkoxy, optionally mono-or di-N—$C_{1-4}$alkyl substituted amino, or optionally substituted $C_5$–$C_7$N-heterocyclyl, preferably optionally substituted $C_5$–$C_7$N-heterocycloalkyl. Most preferably R2 and R3 are, independently of one another, H or optionally substituted (piperazine, pyridine, pyrimidine, morpholine, morpholinylethoxy, ethynyl, prop-1-ynyl) or 3-amino-3-methyl-1-butyne, wherein the optional substituents are as defined above.

When R2 and R3 are linked to form a heterocylic ring this preferably an imidazole ring optionally substituted by 1 or 2 substituents, separately selected from $C_{1-4}$alkyl, halogen, hydroxy, $C_{1-4}$alkoxy, or optionally mono-or di-N—$C_{1-4}$alkyl substituted amino.

A preferred significance for R4 is a dihalo, more preferably difluoro, especially 2,4-difluoro.

Thus in preferred embodiments the invention provides compounds of Formulae II and III

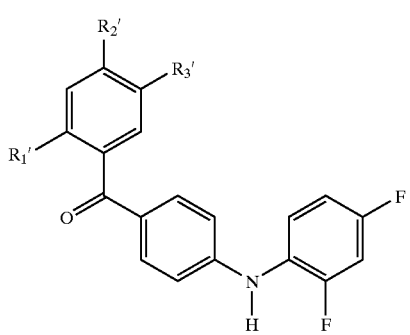

-continued

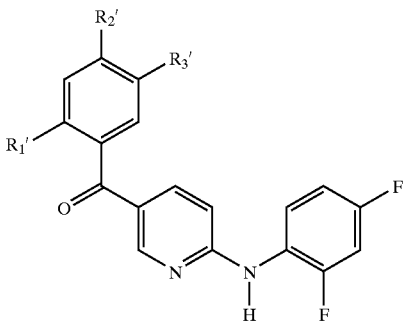

III

Wherein
R1' is halo, $C_1$-$C_4$ lower alkyl, $C_1$-$C_4$ lower alkoxy or halo-substituted $C_1$-$C_4$ lower alkyl;
R2' and R3' are, independently of one another, H or optionally substituted ($C_1$-$C_7$alkenyl, $C_1$-$C_7$alkynyl, $C_5$-$C_7$N-heterocyclyl $C_1$-$C_4$lower alkoxy, $C_5$-$C_7$N-heterocyclyl) wherein the $C_5$-$C_7$N-heterocyclyl optionally contains a further hetero atom, e.g. N or O, and the optional substitution comprises 1 or 2 substituents, separately selected from $C_{1-4}$alkyl, halogen, hydroxy, $C_{1-4}$alkoxy, optionally mono-or di-N—$C_{1-4}$alkyl substituted amino, or optionally substituted $C_5$-$C_7$N-heterocyclyl, or
R2' and R3' are linked to form an imidazole ring optionally substituted by 1 or 2 substituents, separately selected from $C_{1-4}$alkyl, halogen, hydroxy, $C_{1-4}$alkoxy, or optionally mono-or di-N—$C_{1-4}$alkyl substituted amino;
or a pharmaceutically-acceptable and -cleavable ester or acid addition salt thereof.

When R2' or R3' are optionally substituted by $C_5$-$C_7$N-heterocyclyl, the $C_5$-$C_7$N-heterocyclyl, preferably $C_5$-$C_7$N-heterocycloalkyl, is optionally further substituted by 1 or 2 substituents selected from halo, OH, CN, lower alkyl, lower alkoxy, heterocyclyl or NR5R6 where R5 and R6 are as defined above.

In particular the invention includes the following compounds:
(2-Chloro-phenyl)-[4-(2,4-difluoro-phenylamino)-phenyl]-methanone;
[4-(2,4-Difluoro-phenylamino)-phenyl]-(2-methoxy-phenyl)-methanone;
(2-Chloro-5-pyridin-4-yl-phenyl)-[4-(2,4-difluoro-phenylamino)-phenyl]-methanone;
[2-Chloro-4-(2-morpholin-4-yl-ethoxy)-phenyl]-[4-(2,4-difluoro-phenylamino)-phenyl]-methanone;
[5-(3-Amino-3-methyl-but-1-ynyl)-2-methoxy-phenyl]-[4-(2,4-difluoro-phenylamino)-phenyl]-methanone;
[4-(2,4-Difluoro-phenylamino)-phenyl]-[5-(3-dimethylamino-prop-1-ynyl)-2-methoxy-phenyl]-methanone;
[4-(2,4-Difluoro-phenylamino)-phenyl]-[2-methoxy-5-(3-morpholin-4-yl-prop-1-ynyl)-phenyl]-methanone;
[4-(2,4-Difluoro-phenylamino)-phenyl]-{2-methoxy-5-[3-(4-methyl-piperazin-1-yl)-prop-1-ynyl]-phenyl}-methanone;
[4-(2,4-Difluoro-phenylamino)-phenyl]-[2-methoxy-5-((E)-3-morpholin-4-yl-propenyl)-phenyl]-methanone;
[4-(2,4-Difluoro-phenylamino)-phenyl]-[5-((E)-3-dimethylamino-propenyl)-2-methoxy-phenyl]-methanone
[6-(2,4-Difluoro-phenylamino)-pyridin-3-yl]-(2-methoxy-5-pyridin-2-yl-phenyl)-methanone;
[6-(2,4-Difluoro-phenylamino)-pyridin-3-yl]-[2-methoxy-5-(2-piperazin-1-yl-pyrimidin-4yl)-phenyl]-methanone;
[6-(2,4-Difluoro-phenylamino)-pyridin-3-yl]-[5-(3-dimethylamino-prop-1-ynyl)-2-methoxy-phenyl]-methanone;
[6-(2,4-Difluoro-phenylamino)-pyridin-3-yl]-(2-methoxy-5-pyridin-4-yl-phenyl)-methanone;
[5-(3-Amino-3-methyl-but-1-ynyl)-2-methoxy-phenyl]-[6-(2,4-difluoro-phenylamino)-pyridin-3-yl]-methanone;
(2-Chloro-5-pyridin-4-yl-phenyl)-[6-(2,4-difluoro-phenylamino)-pyridin-3-yl]-methanone;
[5-(3-Amino-3-methyl-but-1-ynyl)-2-chloro-phenyl]-[6-(2,4-difluoro-phenylamino)-pyridin-3-yl]-methanone;
(2-Chloro-4-piperazin-1-yl-phenyl)-[6-(2,4-difluoro-phenylamino)-pyridin-3-yl]-methanone;
(6-Chloro-2-methyl-3.H.-benzoimidazol-5-yl)-[6-(2,4-difluoro-phenylamino)-pyridin-3-yl]-methanone;
[6-(2,4-Difluoro-phenylamino)-pyridin-3-yl]-(6-methoxy-2-methyl-3.H.-benzoimidazol-5-yl)-methanone;
[6-(2,4-Difluoro-phenylamino)-pyridin-3-yl]-[2-methoxy-5-(3-morpholin-4-yl-prop-1-ynyl)-phenyl]-methanone;
[6-(2,4-Difluoro-phenylamino)-pyridin-3-yl]-{2-methoxy-5-[3-(4-methyl-piperazin-1-yl)-prop-1-ynyl]-phenyl}-methanone;
[4-(2,4-Difluoro-phenylamino)-phenyl]-[5-(4-hydroxy-1-methyl-piperidin-4-ylethynyl)-2-methoxy-phenyl]-methanone;
[4-(2,4-Difluoro-phenylamino)-phenyl]-{5-[(E)-2-(4-hydroxy-1-methyl-piperidin-4-yl)-vinyl]-2-methoxy-phenyl}-methanone;
[6-(2,4-Difluoro-phenylamino)-pyridin-3-yl]-[5-(1,2-dimethyl-1.H.-imidazol-4-yl)-2-methoxy-phenyl]-methanone;
or a pharmaceutically-acceptable and -cleavable ester or acid addition salt thereof.

The novel benzoyl compounds of the invention, in particular the compounds of formulae I, II and III and the specific compounds listed above are hereinafter referred to "Agents of the Invention".

The Agents of the Invention which comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding Agents of the Invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

Agents of the Invention may also exist in the form of pharmaceutically acceptable salts, and as such are included within the scope of the invention. Pharmaceutically acceptable salts include acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, propionic, succinic, glycolic, lactic, malic, tartaric, citric, ascorbic, maleic, fumaric, hydroxymaleic, pyruvic, pamoic, methanesulfonic, toluenesulfonic, naphthalenesulfonic, sulfanilic or cyclohexylsulfamic acid; also amino acids, such as arginine and lysine. For compounds of the invention having acidic groups, for example, a free carboxy group, pharmaceutically acceptable salts also represent metal or ammonium salts, such as alkali metal or alkaline earth metal salts, e.g., sodium, potassium, magnesium or calcium salts, as well as ammonium salts, which are formed with ammonia or suitable organic amines.

Agents of the Invention of Formula II may be prepared according to the scheme given below:

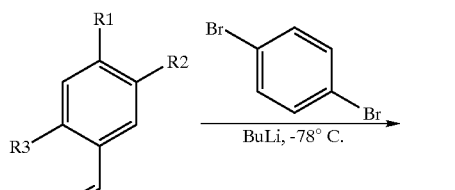

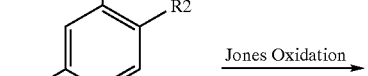

in which the final step involves amination of a 4-bromobenzophenone of formula IV or a Suzuki, Stille or Sonogashira coupling of formula IV'

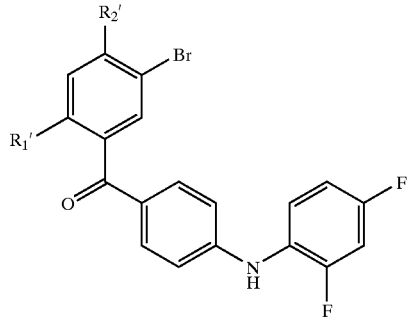

where R1', R2' and R3' are as defined above, with 2,4-difluoroaniline. This amination reaction may be carried out as a Buchwald amination reaction; for instance, in the presence of NaOtBu, Pd(OAc)$_2$ and a suitable catalyst, e.g. R-(+)-BINAP, in a solvent such as dioxan, with heating, e.g. under reflux for about 20 minutes. The 4-bromobenzophenone of formula IV may be prepared by oxidation of the corresponding alcohol of formula V This oxidation may be carried out as a Jones oxidation; for instance, the alcohol dissolved in, e.g. acetone, is treated with Jones reagent for, e.g. about 5 minutes. The alcohol of formula V may be obtained by coupling of 2-chlorobenzaldehyde with 1,4-dibromobenzene; for instance, in the presence of nBuLi.

Agents of the Invention of formula III in which R2" is H and R1', R3' and X are as previously defined may be prepared by coupling of a bromo derivative of formula VI

VI

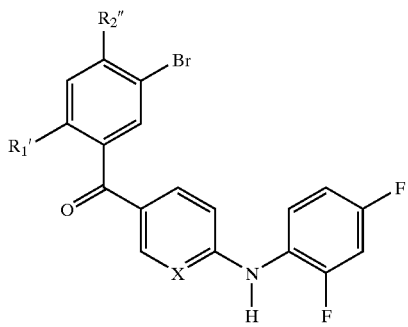

wherein R1', R2" and X are as defined above with a trialkyl tin heteroaryl compound when R3' is heteroaryl or with a lower alkynye compound when R3' is a lower alkynyl substituent. When R3' is heteroaryl the coupling reaction may be effected by heating the compound of formula VI with the trialkyl tin heteroalkyl compound in solution in organic solvent, e.g. xylene, in the presence of a catalyst such as $PdCl_2(PPh_3)_2$. When R3' is a lower alkynyl substituent, the coupling reaction may be effected by heating the compound of formula VI with the lower alkyne compound in solution in an organic solvent, e.g. diisopropylethylamine, in the presence of $PdCl_2(PPh_3)_2$ and CuI.

The compound of formula VI may be prepared by oxidation of the corresponding alcohol of formula VII

VII

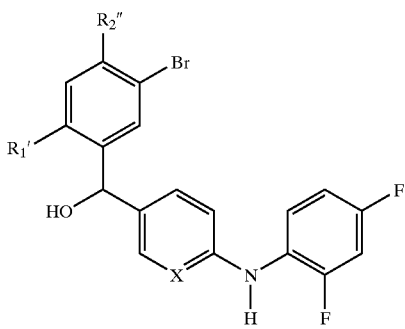

wherein the symbols are as defined above, for example using Jones reagent. The alcohol of formula VII may be prepared by coupling of the (5-bromo-pyridin-2-yl)-(2,4-difluoro-phenyl)-amine or (5-bromophenyl)-(2,4-difluoro-phenyl)-amine with a 5-bromobenzaldehyde compound of formula VIII

VIII

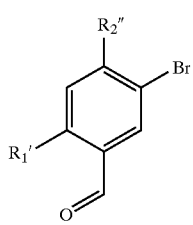

wherein R1' and R2" are as previously defined; for instance, comprising treatment with nBuLi. The (5-bromo-pyridin-2-yl)-(2,4-difluoro-phenyl)-amine reagent may be prepared by coupling of 2,5-dibromopyridine with 2,4-difluoroaniline; for instance, by way of a Buchwald reaction.

Alternatively Agents of the invention of formula IX

IX

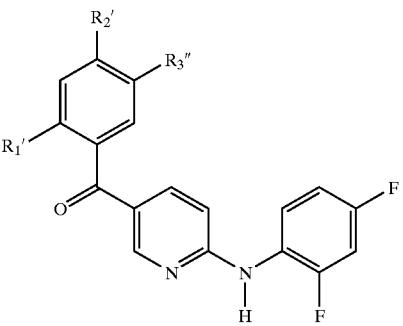

wherein R1' and R2' are as defined above and R3" is H or R2' and R3" are linked together to form an optionally substituted 4- to 6-membered heterocyclic ring as defined above may be prepared by oxidation of the corresponding alcohol of formula X

X

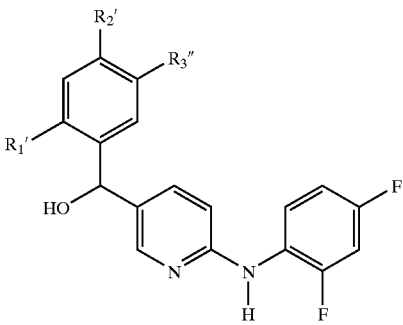

wherein the symbols are as defined above, e.g. by treatment with pyridinium chlorochromate in $CH_2Cl_2$ solution with optional protection of sensitive residues during the oxidation reaction. The alcohol of formula X may be prepared by coupling (5-bromo-pyridin-2-yl)-(2,4-difluoro-phenyl)-amine with a corresponding 5-bromobenzaldehyde compound as described above.

The invention includes processes for the preparation of Agents of the invention of formulae II and III as described above.

Thus in a further aspect the invention provides a process for the preparation of a compound of formula I which comprises
a) amination of a 4-bromobenzophenone of formula IV

IV

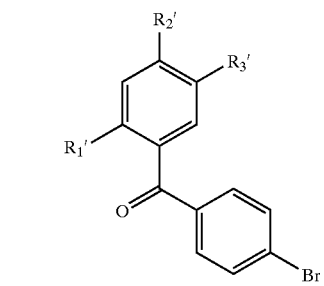

where R1', R2' and R3' are as defined above, with 2,4-difluoroaniline;

b) for the preparation of an Agent of the Invention of formula III

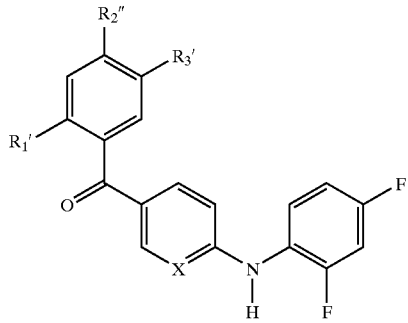

III in which R2" is H and R1', R3' and X are as previously defined, coupling of a bromo derivative of formula VI

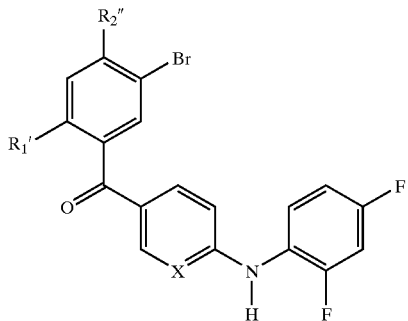

VI wherein R1', R2" and X are as defined above with a trialkyl tin heteroaryl compound when R3' is heteroaryl or with a lower alkynyl or alkenyl compound when R3' is a lower alkynyl or alkenyl substituent, and c) for the preparation of an Agent of the Invention of formula IX

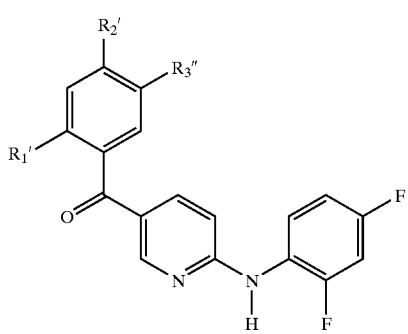

IX wherein R1' and R2' are as defined above and R3" is H or R2' and R3" are linked together to form an optionally substituted 4- to 6-membered heterocyclic ring as defined above, by oxidation of the corresponding alcohol of formula X

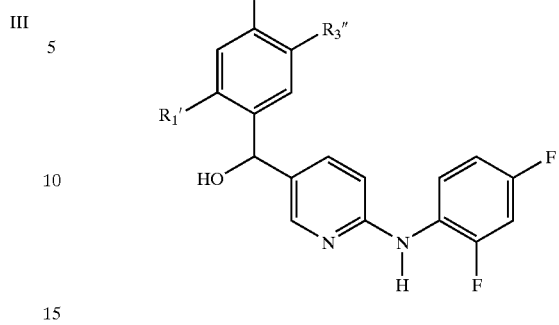

X wherein the symbols are as defined above.

The invention is further described by way of illustration only in the following non-limiting Examples which describe the preparation of Agents of the Invention.

EXAMPLES

The general synthesis of benzophenones of formula II is exemplified in Example 1 by the preparation of 4-(2,4-difluorophenylamino)-2'-chlorobenzophenone starting from commercially available 2-chlorobenzaldehyde. Other compounds of formula II (examples 2–4) are prepared accordingly.

Example 1

(2-Chloro-phenyl)-[4-(2,4-difluoro-phenylamino)-phenyl]-methanone a) (4-Bromo-phenyl)-(2-chloro-phenyl)-methanol

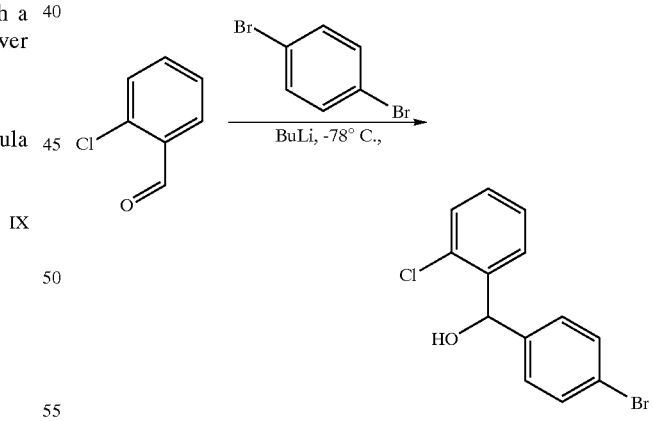

1,4-Dibromobenzene (1 g; 4.2 mmol) is dissolved in THF (30 ml) and treated at −78° C. with nBuLi (2.6 ml of a 1.6M solution in hexanes; 4.2 mmol). After stirring for 5 min at −78° C., 2-chlorobenzaldehyde (1 g; 4.2 mmol) dissolved in THF (0.5 ml) is added dropwise and stirred for another 10 min at −78° C. The raection mixture is poured on water and extracted twice with tert.butyl methyl ether (TBME). The combined organic phases are dried over $Na_2SO_4$, evaporated to dryness (1.3 g) and used without further purification in the next step.

b) (4-Bromo-phenyl)-(2-chloro-phenyl-methanone

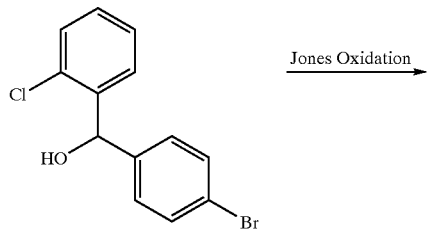

The crude alcohol from the previous step (1.3 g; 4.2 mmol) is dissolved in acetone (40 ml) and treated with Jones reagent (4 ml of a 2.1M solution; 8.4 mmol) (1). After 5 min the reaction mixture is diluted with hexanes (40 ml) and purified via chromatography (SiO2; acetone:hexanes 3:7) to yield the title compound as colorless crystals (590 mg; 47% over 2 steps).

1H-NMR (400 MHz; CDCl$_3$): 7.43 (bt, 2H); 7.52 (bt, 2H); 7.68 (d, 2H); 7.72 (d, 2H). MS (m/z) EI: 296 (M+, 100); 185 (100); 183 (100); 139 (100).

(1) *Fieser & Fieser I,* p. 142 c) (2-Chloro-phenyl)-[4-(2,4-difluoro-phenylamino)-phenyl]-methanone

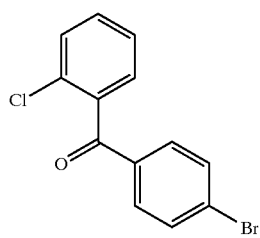

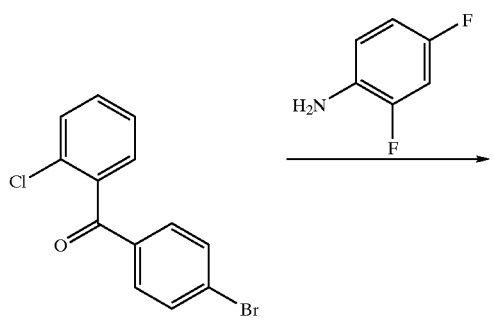

2,4-Difluoroaniline (0.28 ml; 2.7 mmol), NaOtBu (260 mg; 2.7 mmol), Pd(OAc)2 (10 mg; 0.04 mmol), R-(+)-BINAP (10 mg; 0.02 mmol) and (4-bromo-phenyl)-(2-chloro-phenyl)-methanone (200 mg; 0.67 mmol) are dissolved in dioxan (3 ml) and refluxed for 20 min. The reaction mixture is poured on water and extracted with TBME twice. The combined organic phases are dried over Na$_2$SO$_4$, evaporated to dryness and purified via chromatography (SiO$_2$; TBME/hexanes 5/95>2/8) to yield the title compound (103 mg; 44%) as brownish crystals. Recrystallisation from acetone hexanes yields colorless crystals (48 mg; 21%).

1H-NMR (400 MHz; DMSO): 6.83 (d, 2H); 7.13 (bt, 1H); 7.37–7.61 (m, 8H); 8.78 (s, 1H, NH). MS (m/z) Cm: 342 (M−1; 100).

The compounds of Examples 24 are analogously prepared:

Example 2

[4-(2,4-Difluoro-phenylamino)-phenyl]-(2-methoxy-phenyl-methanone

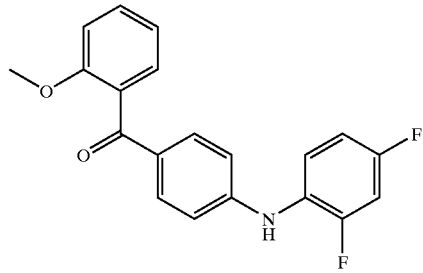

1H-NMR (400 MHz; DMSO): 3.70 (s, 3H); 6.78 (d, 2H); 7.03–7.26 (m, 4H; 7.33–7.50 (m, 3H); 7.54 (d, 2H); 8.62 (s, 1H, NH). MS (m/z) Cm: 362 (M+Na; 100); 340 (NH+; 20); 268 (40).

Example 3

(2-Chloro-5-pyridin-4-yl-phenyl)-[4-(2,4-difluoro-phenylamino)-phenyl]-methanone

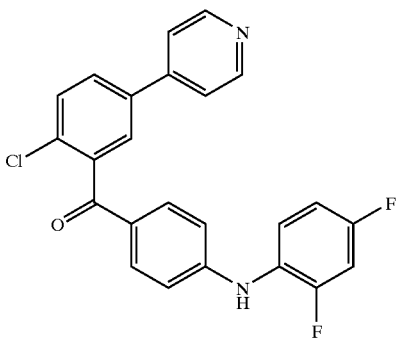

1H-NMR (500 MHz; DMSO): 6.84 (d, 2H); 7.12 (dt, 1H); 7.35–7.45 (m, 2H); 7.62 (d, 2H); 7.74 (d, 1H); 7.79 (d, 2H); 7.89 (d, 1H); 7.99 (dd, 1H); 8.66 (d, 2H); 8.79 (s, 1H). MS (m/z) Cm: 421 (MH+; 100); 167 (40).

Example 4

[2-Chloro-4-(2-morpholin-4-yl-ethoxy)-phenyl]-[4-(2,4-difluoro-phenylamino)-phenyl]-methanone

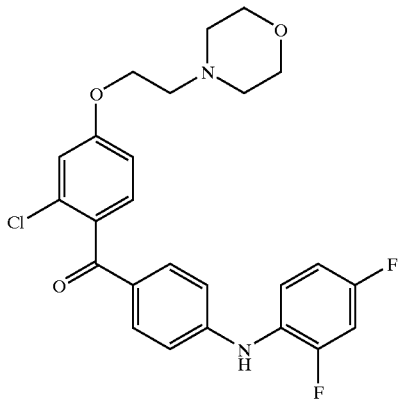

1H-NMR (400 MHz; DMSO): 2.50 (t, 4H); 2.72 (t, 2H); 3.61 (t, 4H); 4.19 (t, 2H); 6.81 (d, 2H); 7.03 (dd, 1H); 7.08–7.15 (bt, 1H); 7.16 (d, 1H); 7.33 (d, 1H); 7.34–7.48 (m, 2H); 7.55 (d, 2H); 8.71 (s, 1H, NH). MS (m/z) ES+: 473 (MH+; 100); 256 (40).

2-Chloro-5-pyridin-4-yl-benzaldehyde used for the preparation of (2-Chloro-5-pyridin-4-yl-phenyl)-[4-(2,4-difluoro-phenylamino)-phenyl]-methanone in Example 3 is prepared as follows:

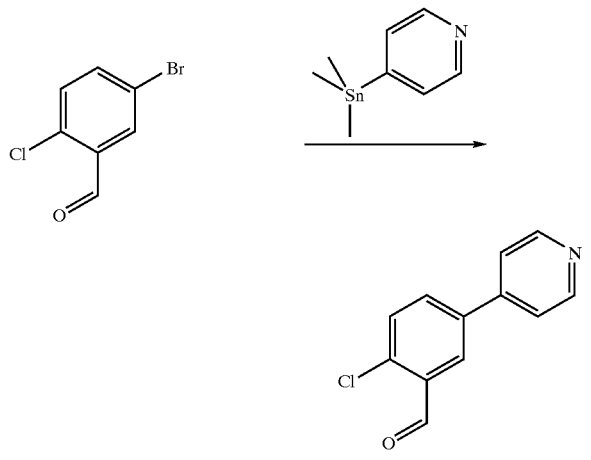

2-Chloro-5-bromobenzaldehyde (2) (0.5 g; 2.27 mmol), 4-trimethylstannylpyridine (3) (0.55 g; 2.27 mmol) and PdCl2(PPh3)2 (0.16 g; 0.227 mmol) are dissolved in xylene and refluxed under argon for 30 min. The reaction mixture is poured onto a column and purified by chromatography (SiO2; TBME/hexanes 6/4>8/2) and yields the title compound as yellowish crystals (0.37 g; 75%)

1H-NMR (400 MHz; DMSO): 7.78 (m, 3H); 8.13 (dd, 1H); 8.23 (d, 1H); 8.69 (d, 2H); 10.40 (s, 1H). MS (m/z) EI: 217 (M+; 100); 215 (90); 188 (20); 153 (30); 126 (25).

(2) Khanna, Ish K. et al. *J. Med. Chem.* (1997), 40(11), 1634–1647.

(3) Phillips, James E.; et al. *J. Organomet. Chem.* (1984), 268(1), 39–47.

2-Chloro-4-(2-morpholin-4-yl-ethoxy)-benzaldehyde used for the preparation of [2-Chloro-4-(2-morpholin-4-yl-ethoxy)-phenyl]-[4-(2,4-difluoro-phenylamino)-phenyl]-methanone in Example 4 is prepared from commercially available 2-chloro-4-hydroxybenzaldehyde (Apin Chemicals):

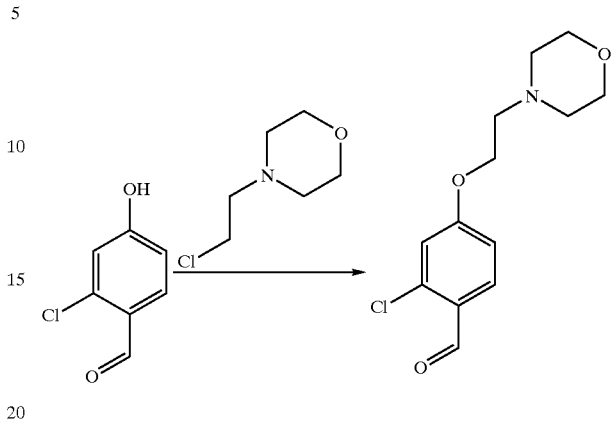

2-Chloro-4-hydroxybenzaldehyde (Apin Chemicals) (0.5 g; 3.2 mmol), N-(2-chloroethyl)morpholin HCl (0.6 g; 3.2 mmol) and K2CO3 (0.97 g; 7 mmol) are refluxed in acetonitrile (3.5 ml) for 4 hours. The reaction mixture is poured on 2N HCl and washed twice with TBME. The aqueous phase is made basic with NaHCO3 and extracted with ethyl acetate three times. The combined organic phases are dried over Na2SO4 and evaporated to dryness. The crude product is purified by filtration over SiO2 (acetone/hexanes 1:1) to yield the title compound as a yellow oil (0.65 g; 75%).

1H-NMR (400 MHz; DMSO): 2.50 (t, 4H); 2.72 (t, 2H); 3.58 (t, 4H); 4.27 (t, 2H); 7.11 (dd, 1H); 7.23 (d, 1H); 7.85 (d, 1H); 10.21 (s, 1H). MS (m/z) EI: 269 (M+; 20); 181 (20); 155 (20); 100 (100).

The following Examples describes preparation of Agents of the Invention from intermediate IV' using a Sonogashira, Stille or Suzuki coupling reaction.

Example 5

[5-(3-Amino-3-methyl-but-1-ynyl)-2-methoxy-phenyl]-[4-(2,4-difluoro-phenylamino)-phenyl]-methanone a) (5-Bromo-2-methoxy-phenyl)-(4-bromo-phenyl)-methanol

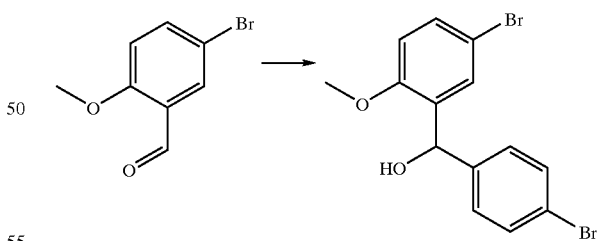

1,4-Dibromobenzene (15.3 g; 65 mmol) in THF (350 ml) is cooled to −78° C. and treated with nBuLi (44.7 ml; 71.5 mmol of a 1.6M solution). The white precipitate is stirred for 15 minutes at −78° C. 5-Bromo-2-methoxy-benzaldehyde (6.98 g; 32.5 mmol) in THF (32 ml) is added, stirred for 5 min at −78° C. and then poured on water. The aqueous phase is extracted twice with TBME, the organic phase dried over Na2SO4, evaporated to dryness and the residue purified via SiO2 chromatography (Cyclohexane/acetone 98:2>96:4) to yield the title compound as white crystals recrystallised from ether/hexanes (9.25 g; 73.8%).

1H-NMR (400 MHz; DMSO-d6): 3.75 (s, 3H); 5.89 (d, 1H); 5.96 (d, 1H); 6.93 (d, 1H); 7.28 (d, 2H); 7.41 (dd, 1H); 7.48 (d, 2H); 7.59 (d, 1H). MS (m/z) EI: 372 (M+, 100); 354 (60); 292 (40); 215 (55); 194 (55).

b) (5-Bromo-2-methoxy-phenyl)-(4-bromo-phenyl)-methanone

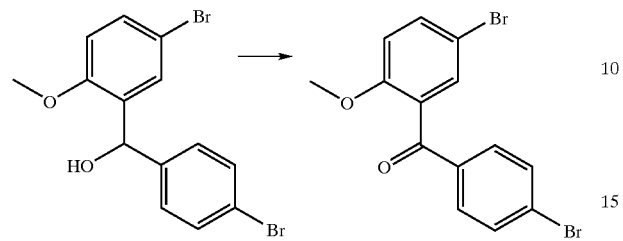

(5-Bromo-2-methoxy-phenyl)-(4-bromo-phenyl)-methanol (37 g; 99.5 mmol) is dissolved in acetone (1400 ml) and treated with Jones reagent (77 ml of a 2.33M solution; 179 mmol) (1) at room temperature for 5 min. The reaction mixture is filtered through a bed of $SiO_2$ and the product obtained as a white solid (33 g; 89%) by eluting with acetone/hexanes (2000 ml; 1:1)

1H-NMR (400 MHz; DMSO-d6): 3.68 (s, 3H); 7.17 (d, 1H); 7.51 (d, 1H); 7.62 (d, 2H); 7.71 (d, 1H); 7.73 (d, 2H). MS (m/z) EI: 370 (M+, 100); 291 (30); 274 (30); 213 (80); 199 (80).

(1) *Fieser & Fieser I*, p. 142 c) (5-Bromo-2-methoxy-phenyl)-[4-(2,4-difluoro-phenylamino)-phenyl]-methanone

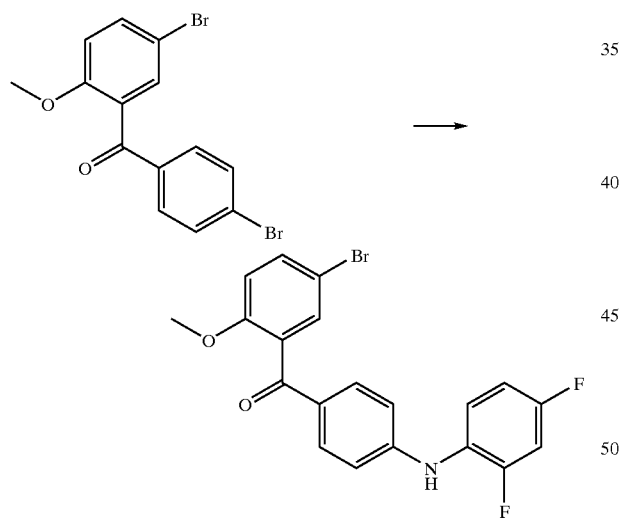

(5-Bromo-2-methoxy-phenyl)-(4-bromo-phenyl)-methanone (16.5 g; 44.6 mmol), R-(+)-BINAP (1.38 g; 2.23 mmol), Pd(OAc)$_2$ (1.499 g; 6.69 mmol), PPh$_3$ (3.03 g; 11.6 mmol), Cs$_2$CO$_3$ (29.1 g; 89.2 mmol) and 2,4-Difluoroaniline (6.8 ml; 66.9 mmol) are dissolved in dioxane (600 ml) and heated to 135° C. for 1.5 hours. The reaction mixture is cooled, filtered, evaporated and purified via chromatography (SiO$_2$; acetone/hexanes 5:95>10:90) to yield the title product as yellow crystals (10.7 g; 57%).

1H-NMR (400 MHz; DMSO-d6):3.71 (s, 3H); 6.80 (d, 2H); 7.10 (qd, 1H); 7.15 (d, 1H); 7.34–7.45 (m, 3H); 7.55 (d, 2H); 7.65 (dd, 1H); 8.68 (s, 1H, NH). MS (m/z) ES-: 418 (M-, 100).

d) [5-(3-Amino-3-methyl-but-1-ynyl)-2-methoxy-phenyl]-[4-(2,4-difluoro-phenylamino)-phenyl]-methanone

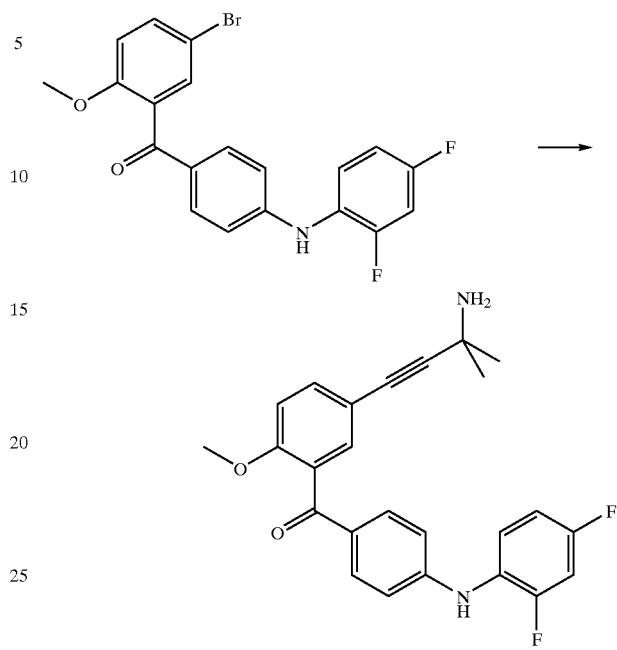

(5-Bromo-2-methoxy-phenyl)-[4-(2,4-difluoro-phenylamino)-phenyl]-methanone (1.43 g; 3.4 mmol) dissolved in N,N-diisopropylethylamine (40 ml), diethylene glycol dimethyl ether (15 ml) and 1,1-dimethyl-prop-2-ynylamine (12.4 ml; 119 mmol), Pd$_2$Cl$_2$(PPh3)$_2$ (0.6 g; 0.6 mmol), Cs$_2$CO$_3$ (2.2 g; 6.8 mmol), CuI (177 mg; 0.9 mmol) are refluxed for 3.5 hours. The reaction mixture is diluted with TBME, filtered, evaporated and purified via chromatography (SiO$_2$, EtOAc/MeOH/NH$_3$conc 98:2:0.2>95:5:0.5) to yield the title compound as a yellow foam (1.1 g; 76%).

1H-NMR (400 MHz; DMSO-d6): 1.36 (s, 6H); 2.03 (bs, 2H); 3.73 (s, 3H); 6.81 (d, 2H); 7.08–7.17 (m, 3H); 7.35–7.48 (m, 3H); 7.53 (d, 2H); 8.67 (s, 1H). MS (m/z) ES-: 419 (M-H-; 50); 171 (100).

Example 6

[4-(2,4-Difluoro-phenylamino)-phenyl]-[5-(3-dimethylamino-prop-1-ynyl -2-methoxy-phenyl]-methanone

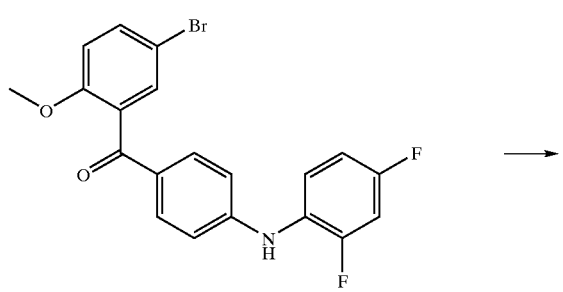

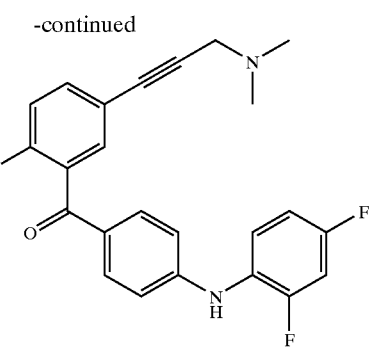

(5-Bromo-2-methoxy-phenyl)-[4-(2,4-difluoro-phenylamino)-phenyl]-methanone (2.88 g; 6.88 mmol), dimethyl-prop-2-ynyl-amine (23 ml; 213 mmol) $PdCl_2(PPh_3)_2$ (920 mg; 1.3 mmol), $Cs_2CO_3$ (5.8 g; 17.9 mmol) and CuI (288 mg; 1.5 mmol) are dissolved in diethylene glycol dimethyl ether (55 ml) and N,N-diisopropylethylamine (28 ml) and heated to 130° C. in an autoclave for 1 hour. The reaction mixture is diluted with TBME, filtered, evaporated and purified by chromatography (1. $SiO_2$, $EtOAc/MeOH/NH_3$conc 100/0/0>97/3/0.3. 2. $SiO_2$, $TBME/MeOH/NH_3$ 100/0/0>95/5/0.5) to yield the title compound as yellow foam (1.12 g; 39%).

1H-NMR (400 MHz; DMSO-d6): 2.22 (s, 6H); 3.41 (s, 2H); 3.72 (s, 3H); 6.80 (d, 2H); 7.10 (bd, 1H); 7.15 (d, 1H); 7.24 (d, 1H); 7.35–7.45 (m, 2H); 7.54 (m, 3H); 8.66 (s, 1H, NH). MS (m/z) ES−: 419 (M−H−; 100).

Example 7

[4-(2,4-Difluoro-phenylamino)-phenyl]-[2-methoxy-5-(3-morpholin-4-yl-prop-1-ynyl)-phenyl]-methanone

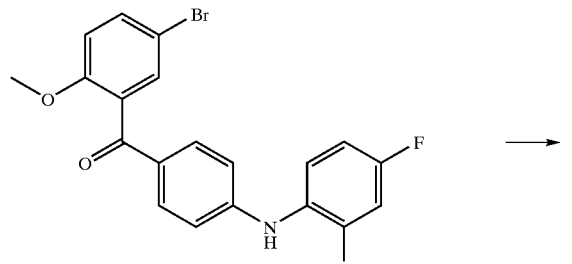

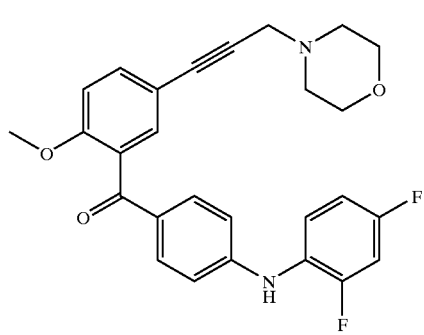

(5-Bromo-2-methoxy-phenyl)-[4-(2,4-difluoro-phenylamino)-phenyl]-methanone (1.00 g; 2.37 mmol), 4-prop-2-ynyl-morpholine (1.2 g; 9.5 mmol) $PdCl_2(PPh_3)_2$ (320 mg; 0.4 mmol), $Cs_2CO_3$ (2.0 g; 6.2 mmol) and CuI (100 mg; 0.52 mmol) are dissolved in diethylene glycol dimethyl ether (10 ml) and N,N-diisopropylethylamine (5 ml) and heated to 140° C. for 1 hour. The reaction mixture is diluted with TBME, filtered, evaporated and purified by chromatography ($SiO_2$, acetone/hexanes 3/7>6/4) to yield the title compound as yellow foam (445 mg; 40%).

1H-NMR (400 MHz; DMSO-d6): 2.52 (s, 4H); 3.50 (s, 2H); 3.62 (bt, 4H); 3.73 (s, 3H); 6.82 (d, 2H); 7.10 (bt, 1H); 7.17 (d, 1H); 7.28 (d, 1H); 7.36–7.47 (m, 2H); 7.53–7.59 (m, 3H); 8.68 (s, 1H, NH). MS (m/z) ES+: 463 (MH+, 100).

Example 8

[4-(2,4-Difluoro-phenylamino)-phenyl]-{2-methoxy-5-[3-(4-methyl-piperazin-1-yl)-prop-1-ynyl]-phenyl}-methanone

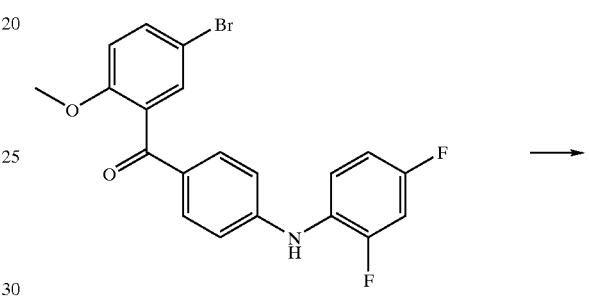

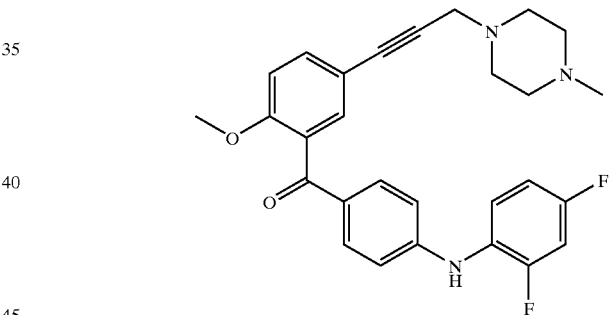

(5-Bromo-2-methoxy-phenyl)-[4-(2,4-difluoro-phenylamino)-phenyl]-methanone (0.5 g; 1.18 mmol), 1-methyl-4-prop-2-ynyl-piperazine (0.33 g; 2.37 mmol), $PdCl_2(PPh_3)_2$ (0.158 g; 0.22 mmol), $Cs_2CO_3$ (1.0 g; 3.1 mmol) and CuI (50 mg; 0.26 mmol) are dissolved in diethylene glycol dimethyl ether (10 ml) and N,N-diisopropylethylamine (5 ml) and heated to 140° C. for 1 hour. The reaction mixture is diluted with TBME, filtered, evaporated and purified by chromatography ($SiO_2$, EtOAc/MeOH/$NH_3$conc 100/0/0>90/10/1) to yield the crude title compound as brown foam. The latter is dissolved in 2N HCl, washed with EtOAc, Na2CO3 added to the aqueous phase and extracted with EtOAc. The organic phase is filtered through Alox and evaporated to give the pure product as yellow foam (177 mg; 32%).

1H-NMR (400 MHz; DMSO-d6): 2.15 (s, 3H); 2.25–2.42 (m, 4H); 2.48–2.58 (m, 4H); 3.46 (s, 2H); 3.72 (s, 3H); 6.81 (d, 2H); 7.10 (bt, 1H); 7.16 (d, 1H); 7.23 (d, 1H); 7.38 (m, 2H); 7.53 (d, 3H); 8.67 (s, 1H, NH). MS (m/z) ES+: 476 (MH+, 100).

Example 9

[4-(2,4-Difluoro-phenylamino)phenyl]-[2-methoxy-5-((E)-3-morpholin-4-yl-propenyl)-phenyl]-methanone

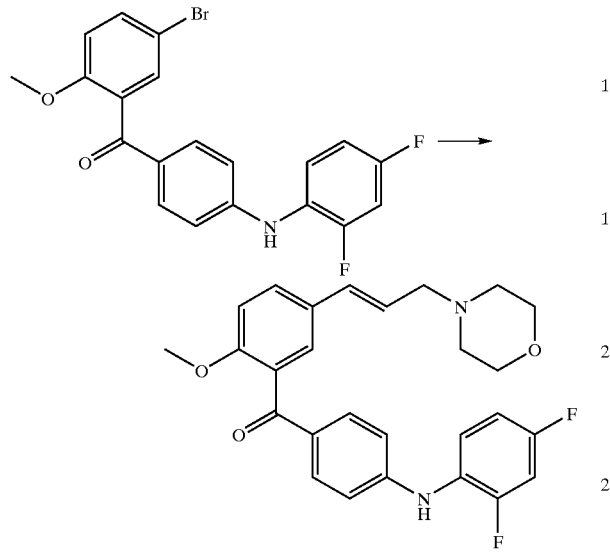

4-((E)-3-Tributylstannanyl-allyl)-morpholine (119 mg, 0.285 mmol) and (5-bromo-2-methoxy-phenyl)-[4-(2,4-difluoro-phenylamino)-phenyl]-methanone (100 mg, 0.237 mmol) are added to a solution of Pd(OAc)$_2$ (5 mg, 0.02 mmol) and PPh$_3$ (25 mg, 0.095 mmol) in diethylene glycol dimethyl ether (4 ml) and heated to 130 C under argon for 40 minutes. The reaction mixture is evaporated to dryness and purified via chromatography (SiO$_2$, acetone/hexanes 1/1>6/4) to yield the crude product, which is dissolved in 2N HCl, washed with TBME and the aqueous phase made alkaline with saturated Na$_2$CO$_3$. Extraction with EtOAc and evaporation of the organic phase delivers the title compound as yellow foam (75 mg; 68%).

1H-NMR (400 MHz; DMSO-d6): 2.37 (bs, 4H); 3.04 (dd, 2H); 3.56 (bt, 4H); 3.69 (s, 3H); 6.18 (dt, 1H); 6.49 (d, 1H); 6.80 (d, 2H); 7.09–7.15 (m, 2H); 7.28 (s, 1H); 7.35–7.45 (m, 2H); 7.53 (d, 3H); 8.63 (s, 1H). MS (m/z) ES+: 465 (MH+, 100).

4-((E)-3-Tributylstannanyl-allyl)-morpholine

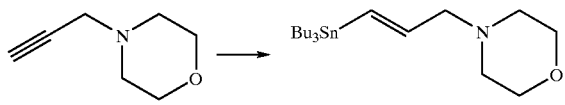

4-Prop-2-ynyl-morpholine (5 g, 40 mmol), PdCl$_2$(PPh$_3$)$_2$ (0.56 g, 0.8 mmol) and Bu$_3$SnH (12.7 ml, 48 mmol) are dissolved in THF (170 ml) and refluxed under argon for 3 hours. The reaction mixture is evaporated and purified via chromatography (acetone/hexanes 0/100>2/98) to yield the title compound as light-brown oil (4.88 g; 29%).

1H-NMR (400 MHz; DMSO-d6): 0.88 (m, 15H); 1.30 (m, 6H); 1.50 (m, 6H); 2.33 (bs, 4H); 3.00 (dd, 2H); 3.58 (dd, 4H); 5.93 (dt, 1H); 6.10 (d, 1H). MS (m/z) ES+: 418 (MH+, 100).

Example 10

[4-(2,4-Difluoro-phenylamino)-phenyl]-[5-((E)-3-dimethylamino-propenyl)-2-methoxy-phenyl]-methanone

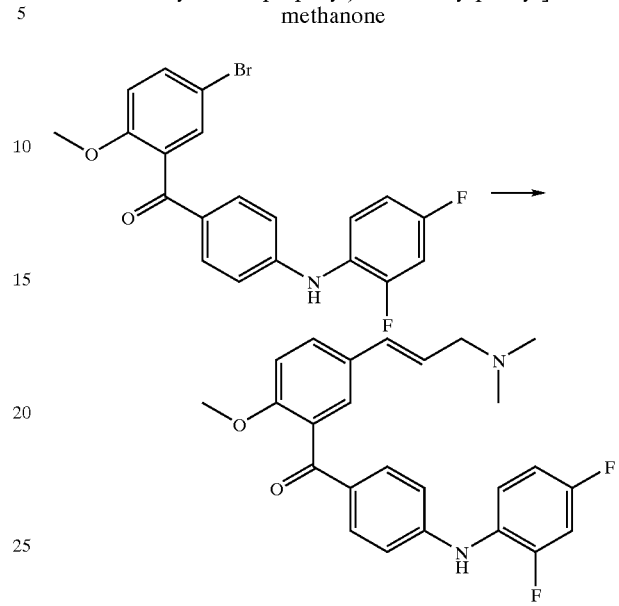

Dimethyl-((E)-3-tributylstannanyl-allyl)-amine (213 mg, 0.57 mmol) and (5-bromo-2-methoxy-phenyl)-[4-(2,4-difluoro-phenylamino)-phenyl]-methanone (200 mg, 0.475 mmol) are added to a solution of Pd(OAc)$_2$ (10 mg, 0.047 mmol) and PPh$_3$ (50 mg, 0.19 mmol) in diethylene glycol dimethyl ether (12 ml) and heated to 135 C under argon for 30 minutes. The reaction mixture is evaporated to dryness and purified via chromatography (SiO$_2$, acetone/hexanes 6/4>1/0 followed by TBME/MeOH/NH$_3$conc 100/0/0>90/10/1) to yield the crude product, which is dissolved in 2N HCl, washed with TBME and the aqueous phase made alkaline with saturated Na$_2$CO$_3$. Extraction with EtOAc and evaporation of the organic phase delivers the title compound, which was dissolved in acetone and filtered through a bed of SiO$_2$ to give the desired product as yellow foam (55 mg; 28%).

1H-NMR (400 MHz; DMSO-d6): 2.21 (s, 6H); 3.07 (bs, 2H); 3.69 (s, 3H); 6.19 (dt, 1H); 6.50 (d, 1H); 6.80 (d, 2H); 7.07 (m, 1H); 7.11 (d, 1H); 7.29 (d, 1H); 7.37–7.48 (m, 2H); 7.53 (d, 3H); 8.63 (s, 1H, NH). MS (m/z) EI: 422 (M+, 100); 407 (60); 379 (20); 352 (15); 232 (90); 203 (25); 173 (25); 70 (50).

Examples 11–21 exemplify the preparation of aroylpyridines of formula III. (5-Bromo-pyridin-2-yl)-(2,4-difluoro-phenyl)-amine is used as the common intermediate for the synthesis of aroylpyridines:

(5-Bromo-pyridin-2-yl)-(2,4-difluoro-phenyl)-amine

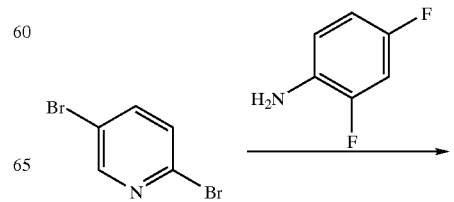

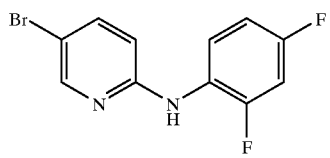

2,5-Dibromopyridine (0.5 g; 2.11 mmol), 2,4-difluoroaniline (0.44 ml; 4.23 mmol), NaOtBu (0.41 g; 4.23 mmol), Pd(OAc)$_2$ (20 mg; 0.08 mmol) and R-(+)BINAP (20 mg; 0.03 mmol) are dissolved in dioxane (6 ml) and refluxed for 30 min. The reaction mixture is poured on a SiO$_2$ column and yields after chromatography (TBME/hexanes 2/8) the title compound (342 mg; 57%) as yellowish crystals.

1H-NMR (400 MHz; DMSO): 6.89 (d, 1H); 7.05 (dt; 1H); 7.28 (dt; 1H); 7.76 (dd, 1H); 7.96 (m, 1H); 8.19 (d, 1H); 8.88 (s, 1H, NH). MS (m/z) EI: 286 (70); 284 (M+; 75); 267 (95); 265 (100); 204 (20); 186 (30).

Example 11

[6-(2,4-Difluoro-phenylamino)-pyridin-3-yl]-(2-methoxy-5-pyridin-2-yl-phenyl)-methanone

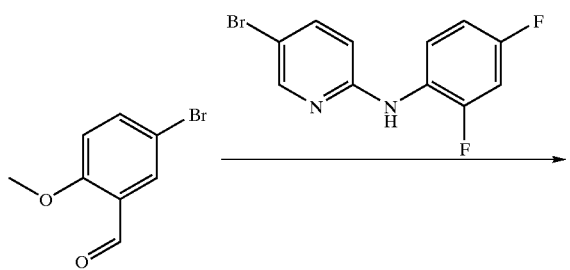

a) (5-Bromo-2-methoxy-phenyl)-[6-(2,4-difluoro-phenylamino)-pyridin-3-yl]-methanol (5-Bromo-pyridin-2-yl)-(2,4-difluoro-phenyl)-amine (100 mg; 0.35 mmol) in THF (2.2 ml) is treated at −78 C with nBuLi (0.48 ml of a 1.5M solution in hexane; 0.77 mmol). After 10 min at −78 C, 5-bromo-2-methoxybenzaldehyde (75 mg; 0.35 mmol) in THF (0.3 ml) is added and stirring continued for 30 min. at −78 C. The reaction mixture is poured on water/ice and extracted three times with ethyl acetate. The combined organic phases are dried over Na$_2$SO$_4$ and evaporated to dryness. Purification via chromatography (SiO$_2$; TBME/hexanes 3/7) yields the title compound (60 mg; 40%)

1H-NMR (400 MHz; DMSO): 3.73 (s, 3H); 5.81 (s, 2H); 6.82 (d, 1H); 6.93 (d, 1H); 7.05 (dt, 1H); 7.25 (dt, 1H); 7.40 (dd, 1H); 7.45 (dd, 1H); 7.65 (d, 1H); 8.00 (d, 1H); 8.03 (m, 1H); 8.60 (s, 1H, NH).

b) (5-Bromo-2-methoxy-phenyl)-[6-(2,4-difluoro-phenylamino)-pyridin-3-yl]-methanone

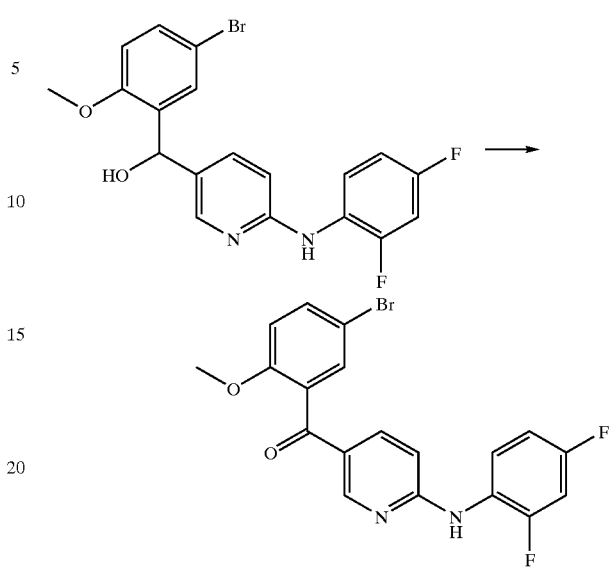

(5-Bromo-2-methoxy-phenyl)-[6-(2,4-difluoro-phenylamino)-pyridin-3-yl]-methanol (980 mg; 2.33 mmol) is dissolved in acetone (22 ml) and treated with Jones reagent (2.33 ml; 5.43 mmol) at room temperature for 15 min. The reaction mixture with a thick yellow precipitate is evaporated, taken up in ethyl acetate and washed with Na$_2$CO$_3$ 2N twice. The organic phase was dried over Na$_2$SO$_4$ and evaporated to dryness. The resulting solid is triturated with ether to render the title compound as slightly colored crystals (740 mg; 75%).

1H-NMR (400 MHz; DMSO):3.72 (s, 3H); 6.89 (d, 1H); 7.10 (bt, 1H); 7.17 (d, 1H); 7.35 (bt, 1H); 7.45 (s, 1H); 7.70 (d, 1H); 7.89 (d, 2H); 8.32 (s, 1H); 9.45 (s, 1H, NM). MS (m/z) Cm: 419 (M+; 90); 417 (100).

c) [6-(2,4-Difluoro-phenylamino)-pyridin-3-yl]-(2-methoxy-5-pyridin-2-yl-phenyl)-methanone

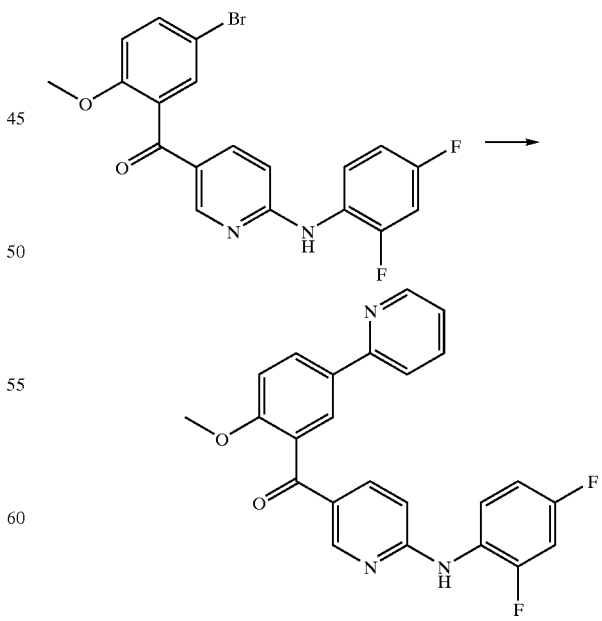

(5-Bromo-2-methoxy-phenyl)-[6-(2,4-difluoro-phenylamino)-pyridin-3-yl]-methanone (50 mg; 0.12 mmol), 2-tributylstannylpyridine (88 mg; 0.26 mmol) and PdCl$_2$(PPh$_3$)$_2$ (25 mg; 0.035 mmol) are dissolved in xylene (2 ml) and refluxed for 4.5 hours. The reaction mixture is diluted with TBME and filtered through a bed of SiO$_2$. The resulting solid is dissolved in ether, crystallized by adding hexanes and yields the title compound as yellowish crystals (20 mg; 40%).

1H-NMR (400 MHz; DMSO): 3.80 (s, 3H); 6.92 (d, 1H); 7.08 (dt, 1H); 7.38–7.48 (m, 3H); 7.82–8.00 (m, 4H); 8.03 (d, 1H); 8.28 (dd, 1H); 8.38 (d, 1H); 8.64 (dd, 1H); 9.44 (s, 1H, NH). MS (m/z) EI: 417 (M+; 100); 398 (90).

Example 12

[6-(2,4-Difluoro-phenylamino)-pyridin-3-yl]-[2-methoxy-5-(2-piperazin-1-yl-pyrimidin-4-yl)-phenyl]-methanone a) [6-(2,4-Difluoro-phenylamino)-pyridin-3-yl]-[2-methoxy-5-(2-methylsulfanyl-pyrimidin-4-yl)-phenyl]-methanone

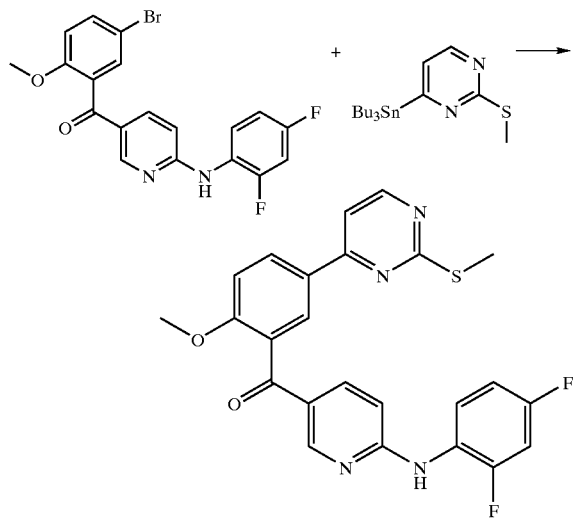

[6-(2,4-Difluoro-phenylamino)-pyridin-3-yl]-[2-methoxy-5-(2-methylsulfanyl-pyrimidin-4-yl)-phenyl]-methanone is prepared in analogy to example 11 from (5-bromo-2-methoxy-phenyl)-[6-(2,4-difluoro-phenylamino)-pyridin-3-yl]-methanone and 2-methylsulfanyl-4-tributylstannanyl-pyrimidine in 45% yield:

1H-NMR (400 MHz; DMSO-d6): 2.56 (s, 3H); 3.82 (s, 3H); 6.91 (d, 1H); 7.07 (dt, 1H); 7.31 (dd, 1H); 7.33 (d, 1H); 7.70 (d, 1H); 7.86–7.96 (m, 2H); 8.13 (d, 1H); 8.35 (d, 1H); 8.38 (dd, 1H); 8.62 (d, 1H); 9.44 (s, 1H, NH). MS (m/z) ES+: 465 (M+, 100)

b) [6-(2,4-Difluoro-phenylamino)-pyridin-3-yl]-[5-(2-methanesulfinyl-pyrimidin-4-yl)-2-methoxy-phenyl]-methanone

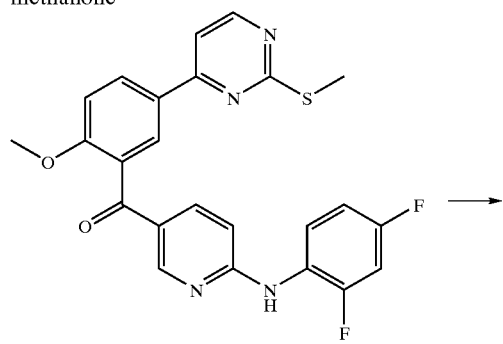

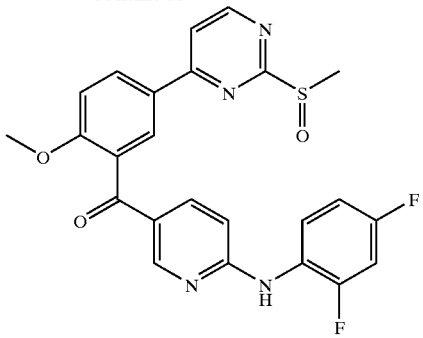

[6-(2,4-Difluoro-phenylamino)-pyridin-3-yl]-[2-methoxy-5-(2-methylsulfanyl-pyrimidin-4-yl)-phenyl]-methanone (565 mg; 1.21 mmol) in methylene chloride (40 ml) was treated at 4 C with mCPBA (77%; 370 mg; 1.5 mmol) for 10 min. The reaction mixture was poured on a silica gel column and purified via chromatography (acetone/hexanes 4/6>9/1) to yield the title compound as yellowish crystals (477 mg; 82%).

1H-NMR (400 MHz; DMSO-d6): 2.92 (s, 3H); 3.84 (s, 3H); 6.92 (d, 1H); 7.07 (dt, 1H); 7.32 (dt, 1H); 7.40 (d, 1H); 7.87–7.93 (m, 1H); 7.92 (dd, 1H); 8.22 (d, 1H); 8.23 (s, 1H); 8.35 (d, 1H); 8.46 (dd, 1H); 8.96 (d, 1H); 9.46 (s, 1H, NH). MS (m/z) ES–: 481 (MH+, 15).

c) [6-(2,4-Difluoro-phenylamino)-pyridin-3-yl]-[2-methoxy-5-(2-piperazin-1-yl-pyrimidin-4-yl)-phenyl]-methanone

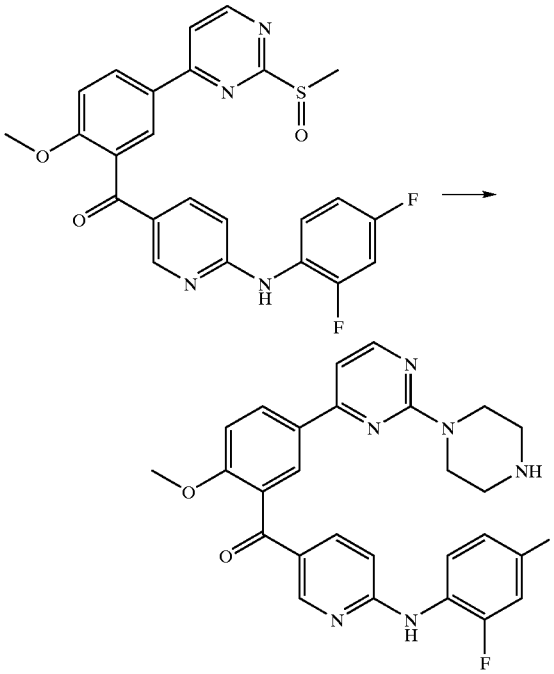

[6-(2,4-Difluoro-phenylamino)-pyridin-3-yl]-[5-(2-methanesulfinyl-pyrimidin-4-yl)-2-methoxy-phenyl]-methanone (1.2 g; 2.5 mmol), piperazine (2 g, 23.2 mmol) in toluene/THF (1:1/50 ml) were heated to 80 C for 30 minutes. The reaction mixture was evaporated and the residue triturated with cold water, taken up in THF/TBME and washed with 1N NaOH followed by water. The organic phase was dried over Na$_2$SO$_4$ and evaporated to dryness. Purification via chromatography (SiO$_2$, TBME/MeOH/

NH₃conc 90/10/1>80/20/2) delivered the desired product as colorless crystals (766 mg; 59%).

1H-NMR (400 MHz; DMSO-d6): 2.74 (bt, 4H); 3.71 (bt, 4H); 3.79 (s, 3H); 6.91 (d, 1H); 7.07 (bt, 1H); 7.17 (d, 1H); 7.25–7.40 (m, 2H); 7.85–7.96 (m, 2H); 8.05 (d, 1H); 8.28 (dd, 1H); 8.34 (d, 1H); 8.38 (d, 1H); 9.43 (s, 1H). MS (m/z) ES+: 503 (MH+, 100).

Example 13

[6-(2,4-Difluoro-phenylamino)-pyridin-3-yl]-[5-(3-dimethylamino-prop-1-ynyl)-2-methoxy-phenyl]-methanone

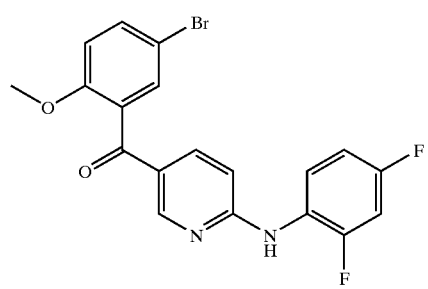

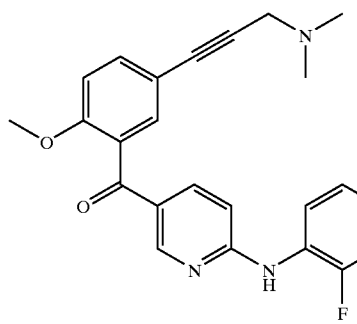

Was prepared in analogy to example 6 above in 40% yield.

1H-NMR (400 MHz; DMSO-d6): 2.22 (s, 6H); 3.42 (s, 2H); 3.73 (s, 3H); 6.89 (d, 1H); 7.08 (bt, 1H); 7.18 (d, 1H); 7.32 (dd, 1H); 7.35 (dd, 1H); 7.56 (dd, 1H); 7.86–7.96 (m, 2H); 8.30 (d, 1H); 9.43 (s, 1H, NH). MS (m/z) ES+: 422 (MH+, 100).

Example 14

[6-(2,4-Difluoro-phenylamino)-pyridin-3-yl]-(2-methoxy-5-pyridin-4-yl-phenyl)-methanone

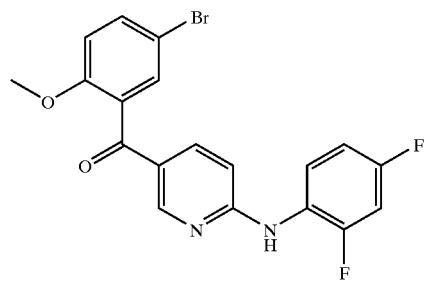

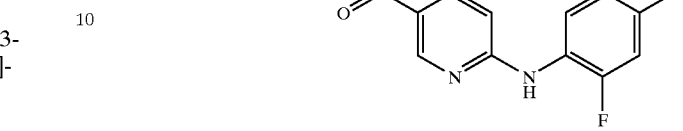

(5-Bromo-2-methoxy-phenyl)-[6-(2,4-difluoro-phenylamino)-pyridin-3-yl]-methanone (100 mg; 0.24 mmol), 4-trimethylstannylpyridine (115 mg; 0.47 mml) and PdCl₂(PPh₃)₂ (50 mg; 0.07 mmol) are dissolved in xylene (2 ml) and refluxed under argon for 20 min. The reaction mixture is purified via chromatography (SiO₂; acetone/hexanes 3/7) and yields the title compound as a colorless foam (32 mg; 32%).

1H-NMR (400 MHz; DMSO): 3.81 (s, 3H); 6.91 (d, 1H); 7.08 (dt, 1H); 7.33–7.36 (m, 2H); 7.74 (dd, 2H); 7.78 (d, 1H); 7.82–7.95 (m, 2H); 8.02 (dd, 1H); 8.37 (1H); 8.60 (d; 2H); 9.44 (s, 1H, NH). MS (m/z) EI: 417 (M+; 100); 398 (70).

Example 15

[5-(3-Amino-3-methyl-but-1-ynyl)-2-methoxy-phenyl]-[6-(2,4-difluoro-phenylamino)-pyridin-3-yl]-methanone

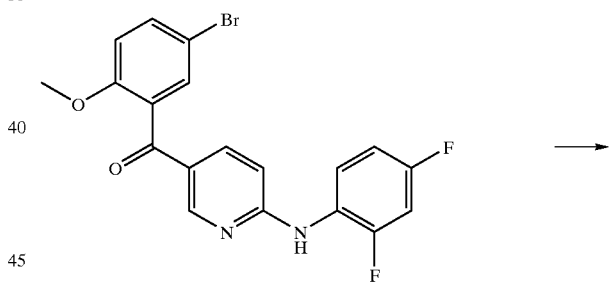

(5-Bromo-2-methoxy-phenyl)-[6-(2,4-difluoro-phenylamino)-pyridin-3-yl]-methanone (1.36 g; 3.2 mmol) is dissolved in hot diisopropylethylamine (120 ml). PdCl₂(PPh₃)₂ (680 mg; 0.97 mmol), Cs₂CO₃ (6.8 g; 0.02 mmol), CuI (0.68 g; 3.57 mmol) and 1,1-dimethyl-prop-2-ynylamine (6.8 ml; 65 mmol) are added and the mixture refluxed under argon for 30 min. The reaction mixture is decanted from the solid, evaporated, taken up in water and extracted three times with ethyl acetate. The combined organic phases are dried over Na$_2$SO$_4$ and evaporated to dryness. Purification via chromatography (SiO$_2$; toluene/ethanol/NH$_3$conc 96/4/0.2>94/6/0.3) yields the title compound as a slightly colored foam (1.14 g; 84%).

1H-NMR (400 MHz; DMSO): 1.36 (s, 6H); 2.05 (bs, 2H, NH2); 3.74 (s, 3H); 6.90 (d, 1H); 7.09 (dt, 1H); 7.16 (d, 1H); 7.24 (d, 1H); 7.34 (dt, 1H); 7.50 (dd, 1H); 7.87–7.92 (m, 2H); 8.30 (d, 1H); 9.44 (s, 1H, NH). MS (m/z) EI: 421 (M+; 30); 406 (100); 404 (70); 194 (40).

Example 16

(2-Chloro-5-pyridin-4-yl-phenyl)-[6-(2,4-difluoro-phenylamino)-pyridin-3-yl]-methanone a) 2-Chloro-5-pyridin-4-yl-benzaldehyde

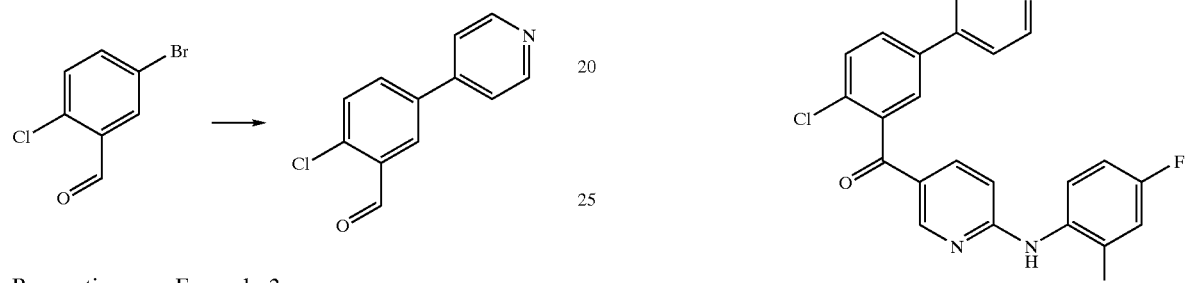

Preparation: see Example 3.

b) (2-Chloro-5-pyridin-4-yl-phenyl)-[6-(2,4-difluoro-phenylamino)-pyridin-3-yl]-methanol

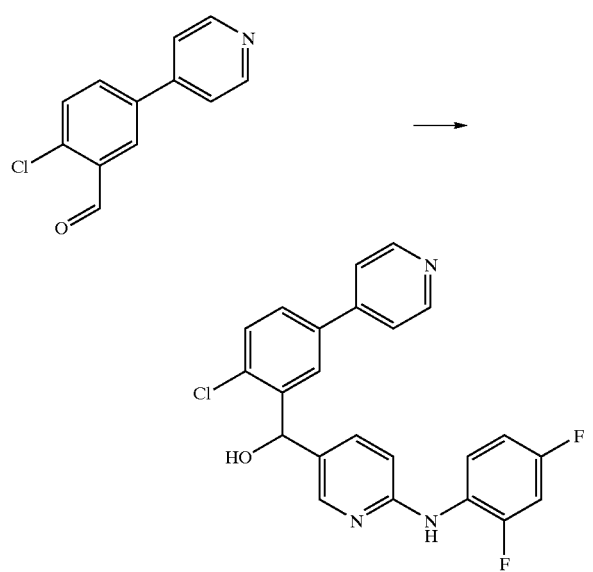

(5-Bromo-pyridin-2-yl)-(2,4-difluoro-phenyl)-amine (170 mg; 0.6 mmol) dissolved in THF (6 ml) is treated at −78 C with nBuLi (0.82 ml of a 1.5 M solution in hexane; 1.3 mmol) for 10 min. 2-Chloro-5-pyridin-4-yl-benzaldehyde (130 mg; 0.6 mmol) in THF (1 ml) is added and stirring continued at −78 C for 10 min. The reaction mixture is then poured on water and extracted with ethyl acetate three times. The combined organic phases are dried over Na$_2$SO$_4$ and evaporated to dryness. Purification via chromatography (SiO$_2$; TBME) yields the title compound as slightly colored foam (111 mg; 44%), containing some residual aldehyde. The compound is submitted in this quality for the next step.

c) (2-Chloro-5-pyridin-4-yl-phenyl)-[6-(2,4-difluoro-phenylamino)-pyridin-3-yl]-methanone

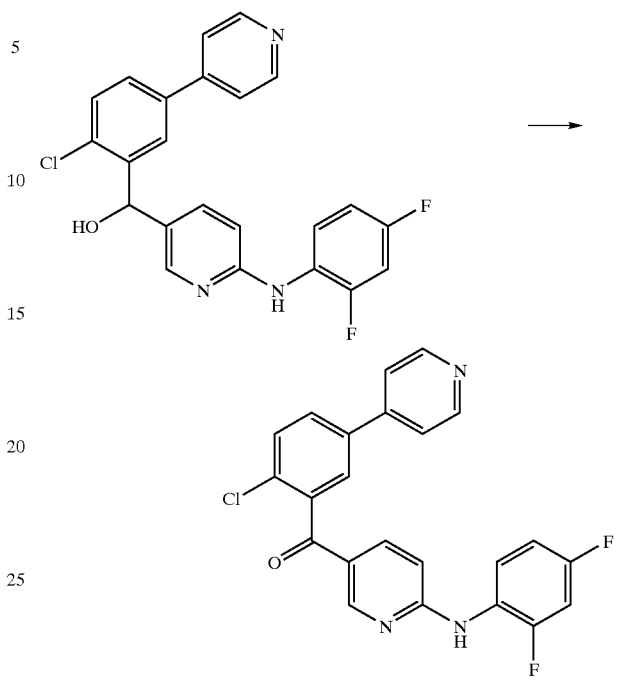

(2-Chloro-5-pyridin-4-yl-phenyl)-[6-(2,4-difluoro-phenylamino)-pyridin-3-yl]-methanol (111 mg; 0.26 mmol) is dissolved in acetone (20 ml) and treated with Jones reagent (0.45 ml; 1 mmol) for 20 min at room temperature. 2N Na$_2$CO$_3$ is added to the reaction mixture and extracted with ethyl acetate three times. The combined organic phases are dried over Na$_2$SO$_4$ and evaporated to dryness. Purification via chromatography (SiO$_2$; CH$_2$Cl$_2$/MeOH 98/2) provides the title compound as a slightly colored foam (30 mg; 27%).

1H-NMR (400 MHz; DMSO): 6.96 (d, 1H); 7.09 (dt, 1H); 7.35 (dt, 1H); 7.75 (d, 1H); 7.81 (d, 2H); 7.83–7.90 (m, 1H); 7.98 (d, 1H); 8.03 (m, 2); 8.3 (d, 1H); 8.67 (d, 2H); 9.55 (s, 1H, NH). MS (m/z) ES+: 422 (MH+; 100); 301 (20); 185 (40).

Example 17

[5-(3-Amino-3-methyl-but-1-ynyl)-2-chloro-phenyl]-[6-(2,4-difluoro-phenylamino)-pyridin-3-yl]-methanone a) (5-Bromo-2-chloro-phenyl)-[6-(2,4-difluoro-phenylamino)-pyridin-3-yl]-methanol

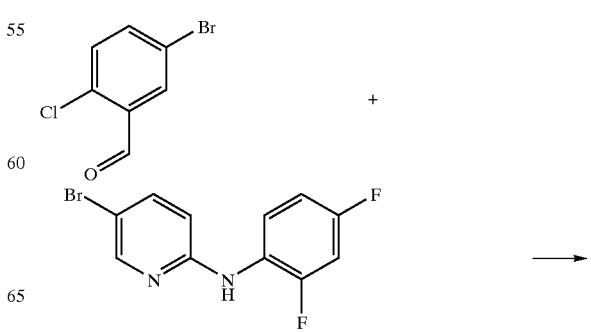

-continued

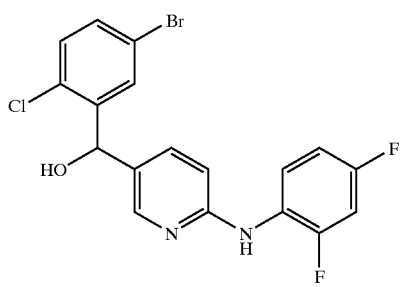

(5-Bromo-pyridin-2-yl)-(2,4-difluoro-phenyl)-amine (3 g; 10.5 mmol) is dissolved in THF (70 ml) and cooled to −78 C. nBuLi (14.5 ml of a 1.5M solution in hexane; 23 mmol) is added dropwise and the resulting yellow suspension stirred or 20 min. 5-Bromo-2-chlorobenzaldehyde in THF (6 ml) is added at −78 C. After 5 min at −78 C, the reaction mixture is warmed to −50 C, poured on water and extracted with TBME twice. The combined organic phases are dried over Na₂SO₄ and evaporated to dryness. Purification via chromatography (SiO₂; acetone/hexanes 6/94>12/88) yields the title compound as orange viscuous oil, (2.58 g; 58%) which is used in the next step.

b) (5-Bromo-2-chloro-phenyl)-[6-(2,4-difluoro-phenylamino)-pyridin-3-yl]-methanone

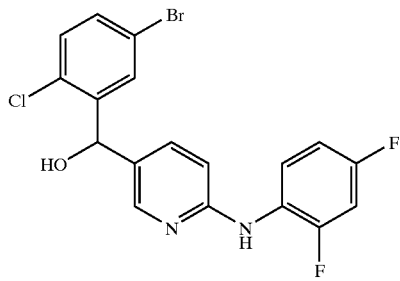

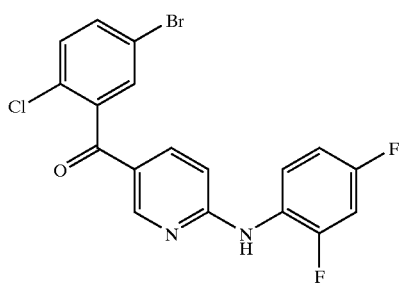

(5-Bromo-2-chloro-phenyl)-[6-(2,4-difluoro-phenylamino)-pyridin-3-yl]-methanol (2.58 g; 6 mmol) is dissolved in acetone (150 ml) and treated with Jones reagent (3.9 ml; 9.1 mmol) for 20 min. The reaction mixture is diluted with hexanes (150 ml) and filtered through a bed of silica gel with acetone/hexanes 1/1 as eluent. After evaporation of the solvent an orange foam results which is recrystallised from TBME/hexanes and yields the title compound as pale orange crystals (1.8 g; 71%).

1H-NMR (400 MHz; DMSO): 6.93 (d, 1H); 7.11 (bt, 1H); 7.35 (bt, 1H); 7.58 (d, 1H); 7.75 (m, 2H); 7.86 (m, 1H); 7.94 (d, 1H); 8.32 (d, 1H); 9.60 (s, 1H, NH). MS (m/z) Cm: 423 (M+100); 421 (70).

c) [5-(3-Amino-3-methyl-but-1-ynyl)-2-chloro-phenyl]-[6-(2,4-difluoro-phenylamino)-pyridin-3-yl]-methanone

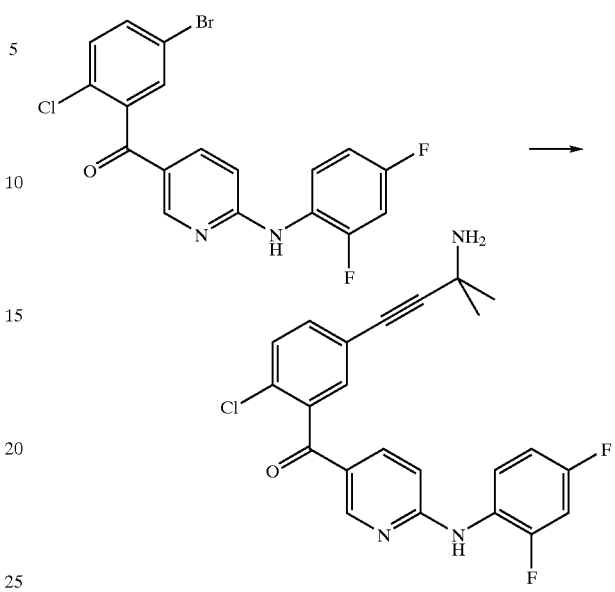

(5-Bromo-2-chloro-phenyl)-[6-(2,4-difluoro-phenylamino)-pyridin-3-yl]-methanone (1.5 g; 3.5 mmol) is dissolved in NEt₃ (110 ml), 3-amino-3-methyl-1-butyne (1.7 ml; 15.9 mmol), CuI (200 mg; 1 mmol), PdCl₂(PPh₃)₂ (250 mg; 0.35 mmol) added and refluxed for 45 min. Since only small amount of product is formed, more PdCl₂(PPh₃)₂ (500 mg; 0.7 mmol), CuI (500 mg; 2.5 mmol) and 3-amino-3-methyl-1-butyne (2 ml; 18.7 mmol) is added and refluxing continued for 2.5 hours. The reaction mixture is decanted, the solvent evaporated and the residue purified by chromatography (SiO₂; toluene/ethanol/NH₃conc 95/5/0.2) to yield the title compound as slightly colored foam (730 mg; 48%).

1H-NMR (400 MHz; DMSO): 1.38 (s, 6H); 2.10 (bs, 2H, NH2); 6.93 (d, 1H); 7.10 (bt, 1H); 7.35 (bt, 1H); 7.45 (d, 1H); 7.52 (d, 1H); 7.58 (d, 1H); 7.87 (m, 1H); 7.93 (dd, 1H); 8.30 (d, 1H); 9.58 (s, 1H, NH). MS (m/z) EI: 425 (M+; 20); 410 (100); 393 (30).

Example 18

(2-Chloro-4-piperazin-1-yl-phenyl)-[6-(2,4-difluoro-phenylamino)-pyridin-3-yl]-methanone a) 4-(3-Chloro-4-formyl-phenyl)-piperazine-1-carboxylic acid ethyl ester

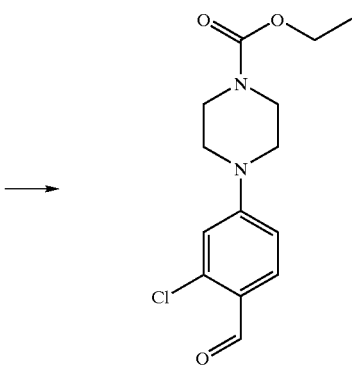

2-Chloro-4-(1-piperazinyl)benzaldehyde (4) (560 mg; 2.5 mmol) is dissolved in THF (20 ml), ClCO2Et (500 mg; 4.5 mmol) and 2N Na₂CO₃ (20 ml) added and the reaction mixture stirred at room temperature for 20 min. The mixture is extracted with TBME three times, the combined organic phases are dried over Na₂SO₄ and evaporated to dryness yielding the title compound as white crystals (700 mg; 94%).

1H-NMR (400 MHz; DMSO): 1.22 (t, 3H); 3.50 (s, 8H); 4.10 (q, 2H); 7.05 (m, 2H); 7.72 (d, 1H); 10.1 (s, 1H). MS (m/z) EI: 296 (M+, 100); 281 (20); 194 (70).

(4) D. Rosi et al. *J. Med Chem.* 1967, 1.0, 877.

b) 4-(3-Chloro-4-{[6-(2,4-difluoro-phenylamino)-pyridin-3-yl]-hydroxy-methyl}-phenyl)-piperazine-1-carboxylic acid ethyl ester

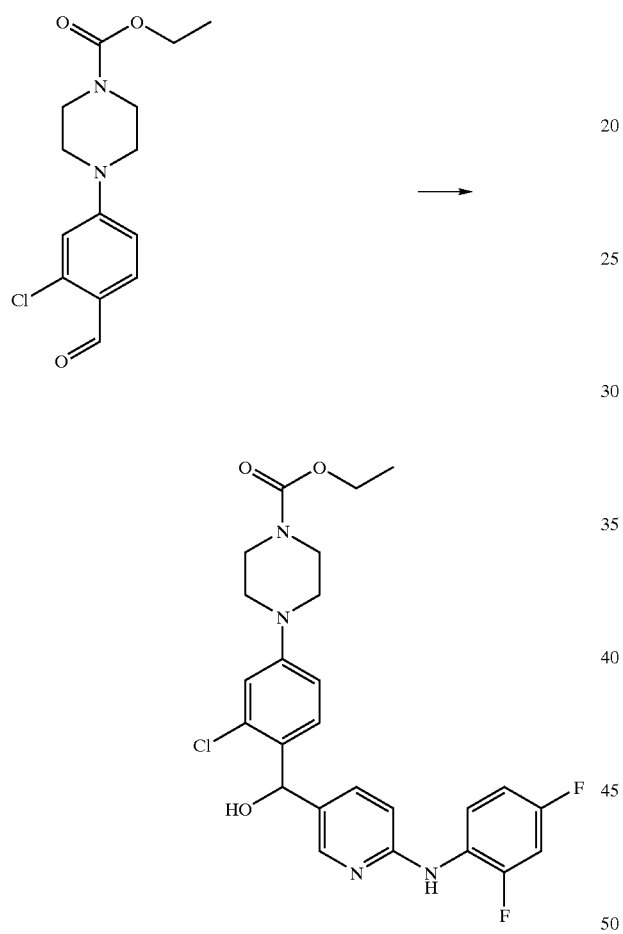

(5-Bromo-pyridin-2-yl)-(2,4-difluoro-phenyl)-amine (310 mg; 1 mmol) is dissolved in THF (7 ml) and cooled to −78 C. nBuLi (1.45 ml of a 1.5M solution in hexane; 2.3 mmol) is added. After stirring for 10 min at −78 C 4-(3-Chloro-4-formyl-phenyl)-piperazine-1-carboxylic acid ethyl ester (300 mg; 1 mmol) in THF (2 ml) is added. The reaction mixture is warmed to −40 C and then poured on water, extracted three times with TBME. The combined organic phases are dried over Na₂SO₄ and evaporated to dryness and purified via chromatography (SiO₂; acetone/hexanes 2/8>3/7) yielding the title compound as slightly yellow foam (216 mg; 41%).

1H-NMR (400 MHz; DMSO): 1.22 (t, 3H); 3.16 (bs, 4H); 3.50 (bs, 4H); 4.09 (q, 2H); 5.82 (s, 2H); 6.83 (d, 1H); 6.93 (s, 1H); 7.05 (bt, 2H); 7.25 (bt, 1H); 7.42 (d, 1H); 7.55 (d, 1H); 8.00–8.10 (m, 2H); 8.61 (s, 1H). MS (m/z) Cm: 503 (MH+; 100); 363 (20).

c) 4-{3-Chloro-4-[6-(2,4-difluoro-phenylamino)-pyridine-3-carbonyl]-phenyl}-piperazine-1-carboxylic acid ethyl ester

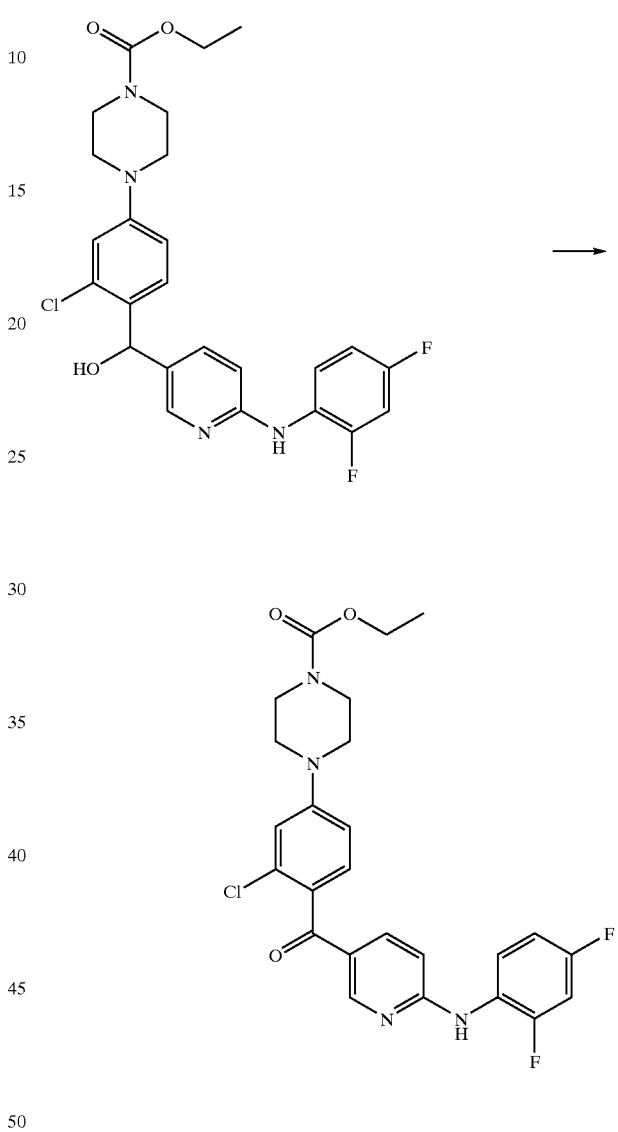

Pyridinium chlorochromate (42 mg; 2 mmol) is added at room temperature to a solution of 4-(3-Chloro-4-{[6-(2,4-difluoro-phenylamino)-pyridin-3-yl]-hydroxy-methyl}-phenyl)-piperazine-1-carboxylic acid ethyl ester (100 mg; 0.2 mmol) in CH₂Cl₂ (2 ml) and stirred for 1 hour. A second portion of pyridinium chlorochromate (42 mg; 2 mmol) is added and stirring continued for 4 hours. The reaction mixture is filtered through cellite and purified by chromatography (SiO2; acetone/hexanes 2/8) yielding the title compound as yellow foam, which crystallises as colorless needles from TBME (32 mg; 33%.

1H-NMR (400 MHz; DMSO): 1.22 (t, 3H); 2.53 (s, 4H); 3.33 (s, 4H); 4.08 (q, 2H); 6.92 (d, 1H); 7.00 (dd, 1H); 7.08 (m, 2H); 7.33 (m, 2H); 7.87 (m, 2H); 8.32 (d, 1H); 9.43 (s, 1H, NH). MS (m/z) Cm: 499 (MH−, 100); 367 (20); 209 (3).

d) (2-Chloro-4-piperazin-1-yl-phenyl)-[6-(2,4-difluoro-phenylamino)-pyridin-3-yl]-methanone

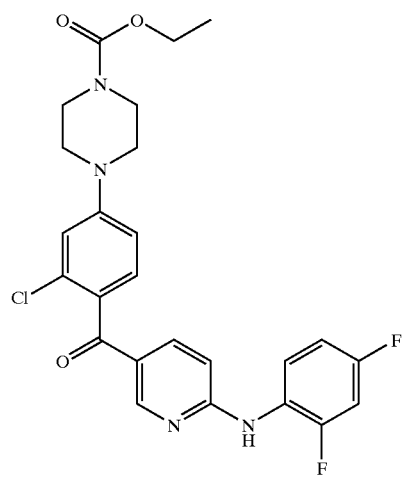

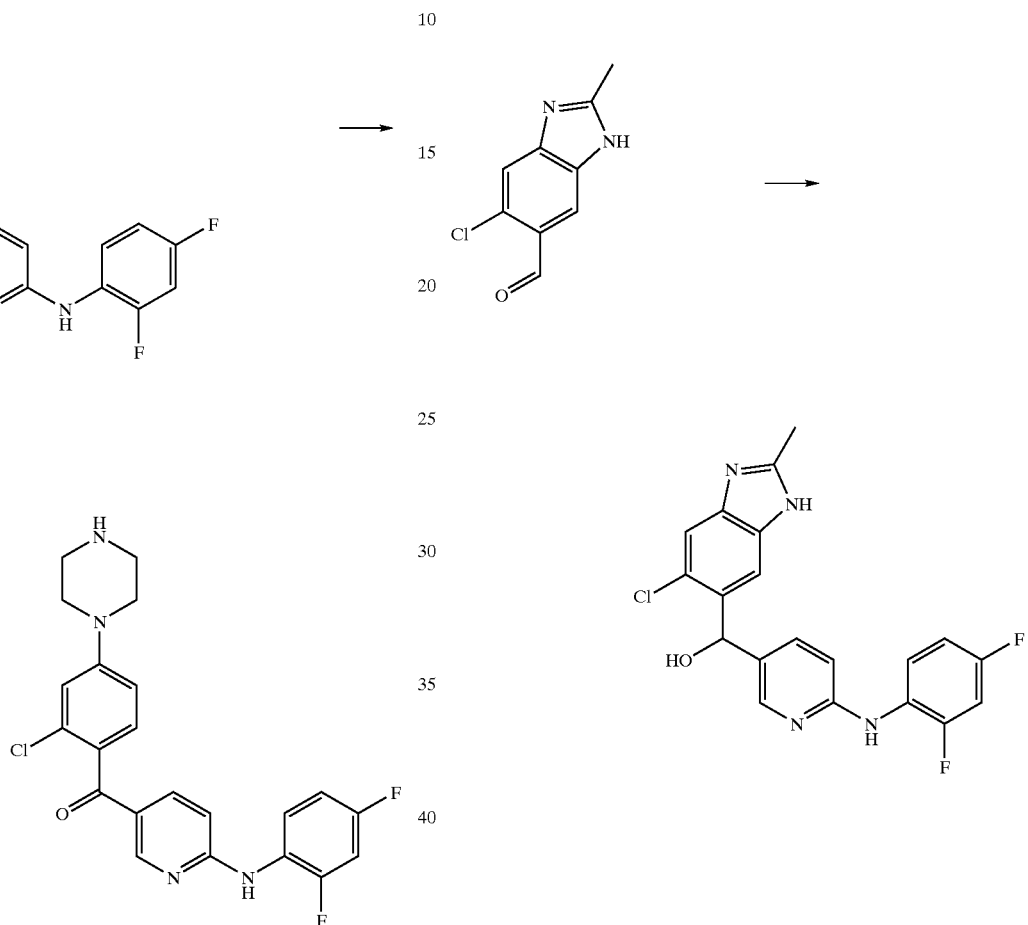

4-{3-Chloro-4-[6-(2,4-difluoro-phenylamino)-pyridine-3-carbonyl]-phenyl}-piperazine-1-carboxylic acid ethyl (45 mg; 0.09 mmol) is dissolved in CHCl₃ and treated with Me₃SiI (0.12 ml; 0.09 mmol) for 5 h at 60 C in a closed vessel under stirring. 2N HCl is added to the reaction mixture and washed twice with ethyl acetate. The HCl-phase is made basic with Na₂CO₃ and extracted with ethyl acetate three times. The combined organic phases are dried over Na₂SO₄, evaporated to dryness and purified via chromatography (SiO₂; TBME/MeOH/NH₃conc 95/5/0.5–80/20/2) to yield the title compound as yellow viscous oil, which turn after trituration with hexanes into a yellow powder (21 mg; 54%)

1H-NMR (400 MHz; DMSO, 120° C.): 2.68 (bt, 2H); 2.90 (bt, 2H); 3.27 (bt, 2H); 3.33 (bt, 2H); 6.87–7.05 (m, 3H); 7.12–7.25 (m, 2H); 7.33 (d, 1H); 7.85–7.90 (m, 2H); 8.37 (s, 1H); 8.87 (bs, 1H, NH). MS (m/z) ES+: 429 (MH+, 100).

Example 19

(6-Chloro-2-methyl-3.H.-benzoimidazol-5-yl)-[6-(2, 4-difluoro-phenylamino)-pyridin-3-yl]-methanone a) (6-Chloro-2-methyl-3.H.-benzoimidazol-5-yl)-[6-(2,4-difluoro-phenylamino)-pyridin-3-yl]-methanol nBuLi (1.31 ml of 1.5M solution in hexane; 2.1 mmol) is added at −78 C to a solution of (5-bromo-pyridin-2-yl)-(2, 4-difluoro-phenyl)-amine (270 mg; 0.95 mmol) in THF (10 ml). After 20 min at −78 C., 6-chloro-5-formyl-2-methylbenzimidazole (5) (90 mg; 0.47 mmol) is added in THF (6 ml) and stirring continued for 10 min at −78 C. The reaction mixture is then poured on water and extracted with ethyl acetate three times. The combined organic phases are dried over Na₂SO₄, evaporated to dryness and purified via chromatography (SiO₂; TBME/MeOH/NH₃conc 100/0/0>95/5/0.5) yielding the title compound as slightly colored foam (166 mg; 89%).

1H-NMR (400 MHz; DMSO; mixture of imidazole tautomers lead to some duplicated signals): 2.50 (s, 3H); 5.96 (bs, 2H); 6.82 (dd; 0.8H); 6.88 (dd, 0.2H); 7.02 (dt, 1H); 7.28 (dt, 1H); 7.41 (bd, 1.6H); 7.50 (bs, 0.4H); 7.74 (s, 0.8H); 7.83 (s, 0.2H); 8.03 (m, 2H); 8.60 (s, 1H); 12.27 (s, 0.2H); 12.36 (s, 0.8H). MS (m/z) Cm: 401 (MH+, 100); 271 (20); 253 (60).

(5) Tanaka, Akito et al. Chem. Pharm. Bull. (1994), 42(3), 560–9.

b) (6-Chloro-2-methyl-3.H.-benzoimidazol-5-yl)-[6-(2,4-difluoro-phenylamino)-pyridin-3-yl]-methanone

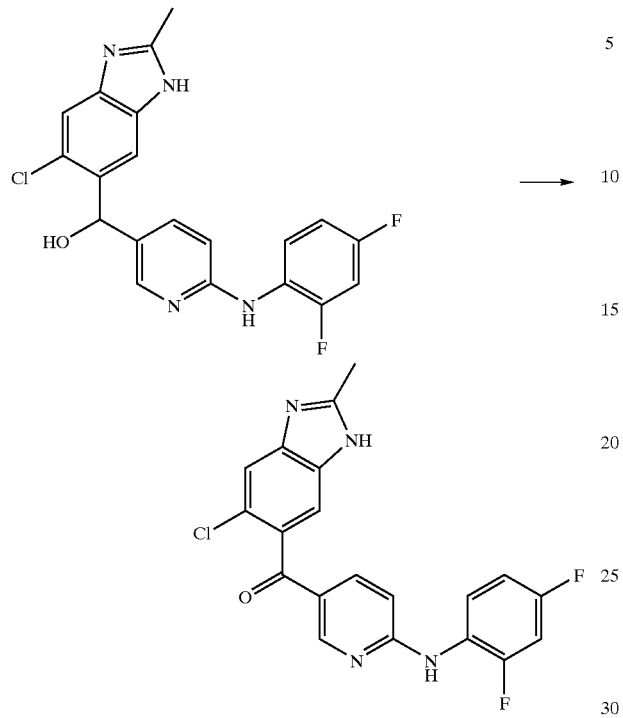

(6-Chloro-2-methyl-3.H.-benzoimidazol-5-yl)-[6-(2,4-difluoro-phenylamino)-pyridin-3-yl]-(160 mg; 0.4 mmol) is dissolved in acetone/water (6 ml 1:1) and treated with Jones reagent (0.34 ml; 0.8 mmol) for 1 hour at room temperature. A second portion of Jones reagent (0.34 ml; 0.8 mmol) is added and stirring continued at 40 C for 1.5 hours. The reaction mixture is poured on water and extracted with ethyl acetate three times. The combined organic phases are dried over $Na_2SO_4$, evaporated to dryness and purified via chromatography ($SiO_2$; TBME/MeOH/$NH_3$conc 98/2/0.2>95/5/0.5) yielding a yellow foam (75 mg) which is dissolved in a small volume of $CH_2Cl_2$ and the product precipitated by the adding TBME and then hexanes as a slightly colored amorphous powder (57 mg; 36%).

1H-NMR (400 MHz; DMSO): 2.54 (s, 3H); 6.92 (d, 1H); 7.08 (dt, 1H); 7.34 (tt, 1H); 7.55 (s, 1H); 7.66 (s, 1H); 7.85–7.95 (m, 2H); 8.31 (d, 1H); 9.48 (s, 1H, NH); 12.59 (s, 1H, NH). MS (m/z) Cm: 397 (MH–; 100).

Example 20

[6-(2,4-Difluoro-phenylamino)-pyridin-3-yl]-(6-methoxy-2-methyl-3.H.-benzoimidazol-5-yl)-methanone

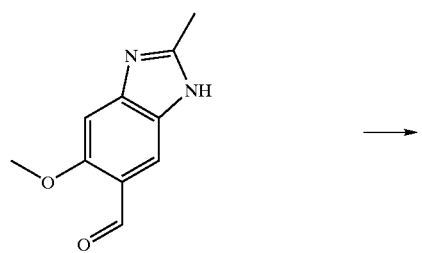

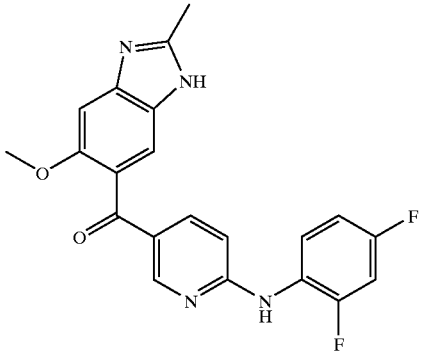

The title compound is prepared analogously to Example 19 from 6-methoxy-2-methyl-3.H.-benzoimidazole-5-carbaldehyde and (5-bromo-pyridin-2-yl)-(2,4-difluoro-phenyl)-amine in two steps and 40% overall yield.

1H-NMR (400 MHz; DMSO-d6): 2.53 (s, 3H); 3.73 (s, 3H); 6.90 (d, 1H); 7.10 (dt, 1H); 7.16 (bs, 1H); 7.32 (dt, 1H); 7.40 (s, 1H); 7.87 (dd, 1H); 7.93 (dd, 1H); 8.33 (d, 1H); 9.34 (bs, 1H, NH); 13.20 (s, 1H, NH). MS (m/z) ES–: 395 (MH+, 100).

Example 21

[6-(2,4-Difluoro-phenylamino)-pyridin-3-yl]-[2-methoxy-5-(3-morpholin-4-yl-prop-1-ynyl)-phenyl]-methanone

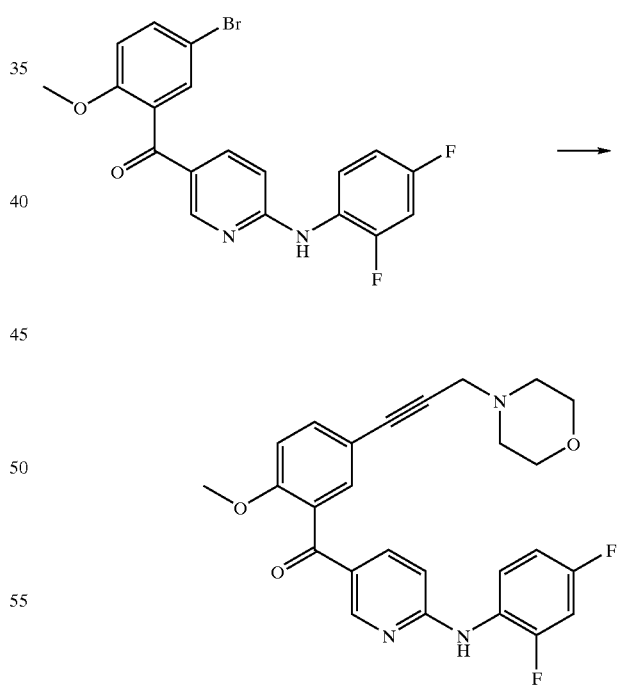

The title compound is prepared in analogously to example 6.

1H-NMR (400 MHz; DMSO-d6): 2.52 (bt, 4H); 3.50 (s, 2H); 3.62 (bt, 4H); 3.75 (s, 3H); 6.90 (d, 1H); 7.08 (bt, 1H); 7.18 (d, 1H); 7.31–7.47 (m, 2H); 7.59 (dd, 1H); 7.85–7.92 (m, 2H); 8.30 (d, 1H); 9.43 (s, 1H, NH). MS (m/z) ES+: 464 (MH+, 100).

Example 22

[6-(2,4-Difluoro-phenylamino)-pyridin-3-yl]-{2-methoxy-5-[3-(4-methyl-piperazin-1-yl)-prop-1-ynyl]-phenyl}-methanone The title compound is prepared in analogously to example 8:

1H-NMR (400 MHz; DMSO-d6): 2.14 (s, 3H); 2.33 (bs, 4H); 2.51 (bs, 4H); 3.46 (s, 2H); 3.73 (s, 3H); 6.87 (d, 1H); 7.07 (bt, 1H); 7.17 (d, 1H); 7.28–7.37 (m, 2H); 7.56 (dd, 1H); 7.82–7.93 (m, 2H); 8.29 (d, 1H); 9.42 (s, 1H, NH). MS (m/z) ES+: 477 (MH+, 100).

Example 23

[4-(2,4-Difluoro-phenylamino)-phenyl]-[5-(4-hydroxy-1-methyl-piperidin-4-ylethynyl)-2-methoxy-phenyl]-methanone The title compound is prepared in analogously to example 8:

1H-NMR (400 MHz; DMSO-d6): 1.67–1.77 (m, 2H); 1.79–1.88 (m, 2H); 2.18 (s, 3H); 2.21–2.30 (m, 2H); 2.48–2.58 (m, 2H); 3.73 (s, 3H); 5.48 (bs, 1H, OH); 6.80 (d, 2H); 7.10 (bt, 1H); 7.17 (d, 1H); 7.21 (d, 1H); 7.32–7.48 (m, 2H); 7.50–7.58 (m, 3H); 8.68 (s, 1H, NH). MS (m/z) ES+: 477 (MH+, 100).

Example 24

[4-(2,4-Difluoro-phenylamino)-phenyl]-{5-[(E)-2-(4-hydroxy-1-methyl-piperidin-4-yl)-vinyl]-2-methoxy-phenyl}-methanone The title compound is prepared analogously to example 9 from (5-bromo-2-methoxy-phenyl)-[4-(2,4-difluoro-phenylamino)-phenyl]-methanone and 1-methyl-4-((E)-2-tributylstannanyl-vinyl)-piperidin-4-ol.

1H-NMR (400 MHz; DMSO-d6): 1.50 (bd, 2H); 1.66 (dt, 2H); 2.15 (s, 3H); 2.27 (bt, 2H); 2.41 (m, 2H); 3.69 (s, 3H); 4.44 (s, 1H, NH); 6.29 (d, 1H); 6.50 (d, 1H); 6.80 (d, 2H); 7.10 (m, 2H); 7.26 (d, 1H); 7.34–7.48 (m, 2H); 7.51 (dd, 1H); 7.56 (d, 2H); 8.63 (s, 1H, NH). MS (m/z) ES+: 479 (MH+, 100).

1-Methyl-4-((E)-2-tributylstannanyl-vinyl)-piperidin-4-ol

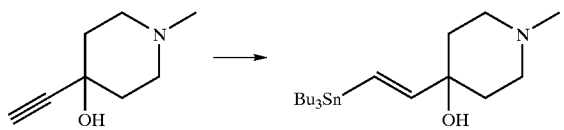

1-Methyl-4-((E)-2-tributylstannanyl-vinyl)-piperidin-4ol is prepared in analogy to the procedure described in example 9 from 4-ethynyl-1-methyl-piperidin-4-ol and Bu3SnH.

1H-NMR (400 MHz; DMSO-d6). 0.88 (m, 15H); 1.30 (m, 6H); 1.40 (m, 2H); 1.50 (m, 6H); 1.60 (m, 2H); 2.15 (s, 3H); 2.27 (bt, 2H); 2.40 (m, 2H); 4.33 (s, 1H, OH); 6.03 (d, 1H); 6.11 (d, 1H). MS (m/z) ES+: 432 (MH+, 100).

Example 25

[6-(2,4-Difluoro-phenylamino)-pyridin-3-yl]-[5-(1,2-dimethyl-1.H.-imidazol-4-yl)-2-methoxy-phenyl]-methanone a) 4-(3-[1,3]Dioxolan-2-yl-4-methoxy-phenyl)-1,2-dimethyl-1.H.-imidazole

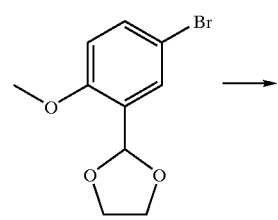

1,2-Dimethyl-1.H.-imidazole (4.8 g, 50 mmol), 2-(5-bromo-2-methoxy-phenyl)-[1,3]dioxolane (6.5 g, 25 mmol), Pd(OAc)₂ (140 mg, 0.625 mmol), PPh₃ (327 mg, 1.25 mmol) and Cs₂CO₃ (8.15 g; 25 mmol) are dissolved in DMF (50 ml) and heated to 145 C for 5 h under argon. The reaction mixture is poured on saturated NaCl-solution and extracted with EtOAc 3 times. The organic phases are dried over Na₂SO₄, evaporated to dryness and purified via chromatography (SiO₂, Acetone/EtOH 9/1) to yield the title compound as a clear oil (4.0 g; 58%).

1H-NMR (400 MHz; DMSO-d6): 2.33 (s, 3H); 3.46 (s, 3H); 3.82 (s, 3H); 3.92 (m, 2H); 4.05 (m, 2H); 6.02 (s, 1H); 6.78 (s, 1H); 7.12 (d, 1H); 7.40 (m, 2H). MS (m/z) ES+: 275 (ME+, 100).

b) 5-(1,2-Dimethyl-1.H.-imidazol-4-yl)-2-methoxy-benzaldehyde

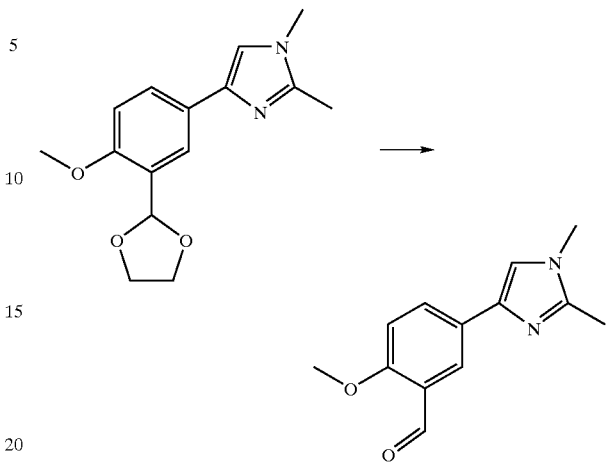

4-(3-[1,3]Dioxolan-2-yl-4-methoxy-phenyl)-1,2-dimethyl-1.H.-imidazole (4.0 g, 14.5 mmol) is dissolved in acetone/H₂SO₄conc (264 ml/3.2 g) and stirred for 3 h at room temperature. Acetone is partially evaporated and the residue dissolved in EtOAc, washed with 2N Na₂CO₃ and water, dried over Na₂SO₄ and evaporated to dryness. The crude product is recrystallised from TBME/hexanes to yield the title compound as colorless crystals (2.8 g, 83%).

1H-NMR (400 MHz; DMSO-d6): 2.34 (s, 3H); 3.49 (s, 3H); 3.96 (s, 3H); 6.85 (s, 1H); 7.34 (d, 1H); 7.66 (d, 1H); 7.73 (dd, 1H); 10.38 (s, 1H). MS (m/z) EI: 230 (M+, 100), 215 (10); 187 (40).:

c) [6-(2,4-Difluoro-phenylamino)-pyridin-3-yl]-[5-(1,2-dimethyl-1.H.-imidazol-4-yl)-2-methoxy-phenyl]-methanone

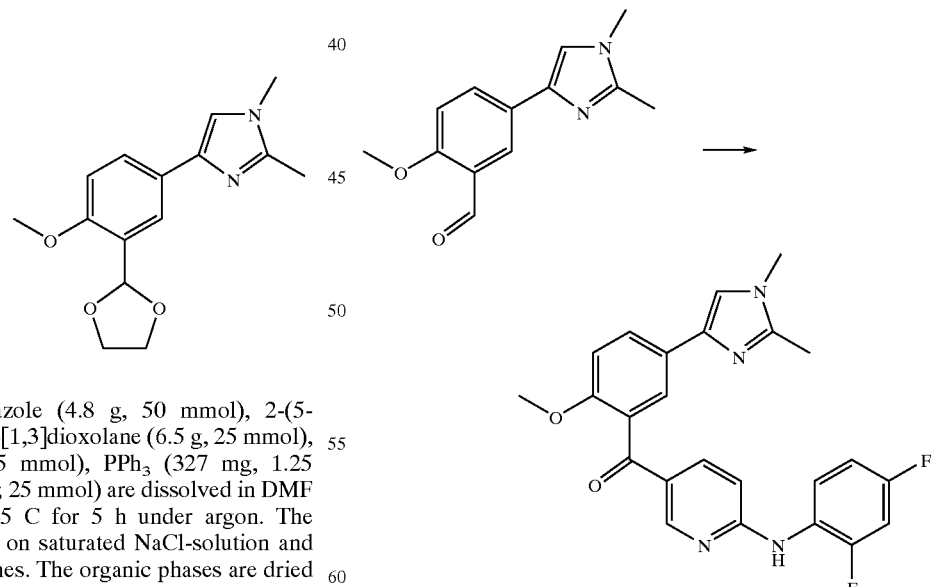

5-(1,2-Dimethyl-1.H.-imidazol-4-yl)-2-methoxy-benzaldehyde is converted according to example 19 in two steps and 42% yield into the target compound:

1H-NMR (400 MHz; DMSO-d6): 2.32 (s, 3H); 3.50 (s, 3H); 3.75 (s, 3H); 6.83 (s, 1H); 6.90 (m, 1H); 7.07 (bt, 1H);

7.26 (d, 1H); 7.29 (d, 1H); 7.33 (m, 1H); 7.53 (dd, 1H); 7.85–7.95 (m, 2H); 8.34 (d, 1H); 9.42 (s, 1H, NM). MS (m/z) EI: 434 (M+, 100); 414 (70); 385 (30).

The Agents of the Invention, as defined above, e.g., of formula I, II and III particularly as exemplified, in free or pharmaceutically acceptable acid addition salt form, exhibit pharmacological activity and are useful as pharmaceuticals, e.g. for therapy, in the treatment of diseases and conditions as hereinafter set forth.

In particular Agents of the Invention possess p38 MAP kinase (Mitogen Activated Protein Kinase) inhibiting activity. Thus the Agents of the Invention act to inhibit production of inflammatory cytokines, such as TNF-α and IL-1, and also to potentially block the effects of these cytokines on their target cells. These and other pharmacological activities of the Agents of the Invention as may be demonstrated in standard test methods for example as described below:

p38 MAP Kinase Assay

The substrate (GST-ATF-2; a fusion protein comprising amino acids 1–109 of ATF-2 and the GST protein obtained by expression in *E. coli*) is coated onto the wells of microtiter plates (50 μl/well; 1 μg/ml in PBS/0.02% Na azide) overnight at 4° C. The following day, the microtiter plates are washed four times with PBS/0.5% Tween 20/0.02% Na azide and are blocked with PBS/2% BSA/0.02% Na Azide for 1 h at 37° C. Plates are washed again 4 times with PBS/0.5% Tween 20/0.02% Na azide. The kinase cascade reaction is then started by adding the following reactants in 10 μl aliquots to a final reaction volume of 50 μl.

1. Agents of the Invention titrated from 10 to 0.001 μM in 10-fold dilutions or solvent (DMSO) or $H_2O$.
2. Kinase buffer (5×); pH 7.4; 125 mM Hepes (Stock at 1M; Gibco #15630-056), 125 mM β-glycerophosphate (Sigma #G-6251):125 mM $MgCl_2$ (Merck #5833); 0.5 mM Sodium orthovanadate (Sigma #5-6508), 10 mM DTT (Boehringer Mannheim #708992). The (5×) kinase buffer must be prepared fresh the day of the assay from 5× stock solutions kept at RT. DTT is kept at −20° C. and is added as the last reagent.
3. His-p38 MAP kinase (10 ng/well; Novartis—a fusion protein comprising full length murine p38 MAP kinase and a His tag, obtained by expression in *E. coli*)
4. cold ATP (final concentration 120 μM; Sigma #A-9187)
5. Water After 1 h at 37° C. the kinase reaction is terminated by washing the plates four times as previously described. Phosphorylated GST-ATF-2 is then detected by adding:

1. the PhosphoPlus ATF-2 (Thr71) Antibody (50 μl/well; 1/1000 final dilution in PBS/2% BSA/0.02% Na Azide; New England Biolabs #9221L) for 90 min at RT.
2. Biotin labelled goat-anti-rabbit IgG (50 μl/well; 1/3000 final dilution in PBS/2% BSA/0.02% Na Azide; Sigma #B-9642) for 90 min at RT.
3. Streptavidin-alkaline phosphatase (50 μl/well; 1/5000 dilution in PBS/2% BSA/0.02% Na Azide; Jackson Immunoresearch #016-050-084 ) for 30 min at RT.
4. Substrate (100 μl/well; Sigma 104 Phosphatase substrate tablets, 5 mg/tablet; #104–105; 1 mg/ml in substrate buffer, Diethanolamine (97 ml/l; Merck #803116)+ $MgCl_2.6H_2O$ (100 mg/l; Merck #5833)+Na Azide (0.2 g/l)+HCl 1M to pH 9.8) 30 min at RT.

After step 1,2 and 3 the microtiter plates are washed four times with PBS/0.5% Tween 20/0.02% Na azide. After step 4, the plates are read in a Bio-Rad microplate reader in a dual wavelength mode (measurement filter 405 nm and reference filter 490 nm). The bachground value (without ATP) is subtracted and $IC_{50}$ values are calculated using the Origin computer program (4 parameter logistic function).

Agents of the Invention typically have $IC_{50}$s for p38 MAP kinase inhibition in the range from about 500 nM to about 5 nM or less when tested in the above assay.

Assay for Inhibition of TNF-α Release from hPBMCs

Human peripheral blood mononuclear cells (hPBMCs) are prepared from the peripheral blood of healthy volunteers using ficoll-hypaque density separation according to the method of Hansell et al., J. Imm. Methods (1991) 145: 105. and used at a concentration of $10^5$ cells/well in RPMI 1640 plus 10% FCS. Cells are incubated with serial dilutions of the test compounds for 30 minutes at 37° C. prior to the addition of IFNg (100 U/ml) and LPS (5 mg/ ml) and subsequently further incubated for three hours. Incubation is terminated by centrifugation at 1400 RPM for 10 min. TNF-α in the supernatant is measured using a commercial ELISA (Innotest hTNFa, available from Innogenetics N.V., Zwijnaarde, Belgium). Agents of the Invention are tested at concentrations of from 0 to 10 mM. Exemplified Agents of the Ivention typically suppress TNF release in this assay with an $IC_{50}$ of from about ? nM to about ? nM or less when tested in this assay.

Assay for Inhibition of TNF-α Production in LPS Stimulated Mice

Injection of lipopolysaccharide (LPS) induces a rapid release of soluble tumour necrosis factor (TNF-α) into the periphery. This model is be used to analyse prospective blockers of TNF release in vivo.

LPS (20 mg/kg) is injected i.v. into OF1 mice (female, 8 week old). One (1) hour later blood is withdrawn from the animals and TNF levels are analysed in the plasma by an ELISA method using an antibody to TNF-α. Using 20 mg/kg of LPS levels of up to 15 ng of TNF-α/ml plasma are usually induced. Compounds to be evaluated are given either orally or s.c. 1 to 4 hours prior to the LPS injection. Inhibition of LPS-induced TNF-release is taken as the readout.

Agents of the Invention typically inhibit TNF production to the extent from about 50% up to about 90% or more in the above assay when administered at 30 mg/kg p.o.

As indicated in the above assays Agents of the Invention are potent inhibitors of TNF-α release. Accordingly, the Novel Compounds have pharmaceutical utility as follows:

Agents of the Invention are useful for the prophylaxis and treatment of diseases or pathological conditions mediated by cytokines such as TNFα and IL-1, e.g., inflammatory conditions, autoimmune diseases, severe infections, and organ or tissue transplant rejection, e.g. for the treatment of recipients of heart, lung, combined heart-lung, liver, kidney, pancreatic, skin or corneal transplants and for the prevention of graft-versus-host disease, such as following bone marrow transplants.

Agents of the Invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which Agents of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Agents of the Invention are also useful for the treatment, prevention, or amelioration of asthma, bronchitis, pneumoconiosis, pulmonary emphysema, and other obstructive or inflammatory diseases of the airways.

Agents of the Invention are useful for treating undesirable acute and hyperacute inflammatory reactions which are mediated by TNF, especially by TNFα, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

Agents of the Invention are also useful for the treatment of neurodegenerative diseases, such as Alzheimer's disease, acute encephalitis, brain injury, multiple sclerosis including demyelation and oligiodendrocyte loss in multiple sclerosis and inflammatory nervous system diseases, such as neuroinflammatory and stroke.

Agents of the Invention are particularly useful for treating diseases of bone metabolism including osteoarthritis, osteoporosis and other inflammatory arthritides.

For the above indications the appropriate dosage will, of course, vary depending, for example, on the particular Agent of the Invention employed, the subject to be treated, the mode of administration and the nature and severity of the condition being treated. However, in general, satisfactory results in animals are obtained at daily dosages of from about 1 to about 10 mg/kg/day p.o. In larger mammals, for example humans, an indicated daily dosage is in the range of from about 50 to about 750 mg of an Agent of the Invention administered orally once or, more suitably, in divided dosages two to four times/day.

The Agents of the Invention may be administered by any conventional route, e.g. orally, for example in the form of solutions for drinking, tablets or capsules or parenterally, for example in the form of injectable solutions or suspensions. Normally for systemic administration oral dosage forms are preferred, although for some indications the Agents of the Invention may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral administration comprise e.g. from 25 to 250 mg of Agent of the Invention per unit dosage.

In accordance with the foregoing the present invention also provides in a further series of embodiments:

A. A method of inhibiting production of soluble TNF, especially TNFα, or of reducing inflammation in a subject (i.e., a mammal, especially a human) in need of such treatment which method comprises administering to said subject an effective amount of an Agent of the Invention, or a method of treating any of the above mentioned conditions, particularly a method of treating an inflammatory or autoimmune disease or condition, e.g. rheumatoid arthritis, or alleviating one or more symptoms of any of the above mentioned conditions.

B. An Agent of the Invention for use as a pharmaceutical, e.g. for use as an immunosuppressant or antiinflammatory agent or for use in the prevention, amelioration or treatment of any disease or condition as described above, e.g., an autoimmune or inflammatory disease or condition.

C. A pharmaceutical composition comprising an Agent of the Invention in association with a pharmaceutically acceptable diluent or carrier, e.g., for use as an immunosuppressant or anti-inflammatory agent or for use in the prevention, amelioration or treatment of any disease or condition as described above, e.g., an autoimmune or inflammatory disease or condition.

D. Use of an Agent of the Invention in the manufacture of a medicament for use as an immunosuppressant or anti-inflammatory agent or for use in the prevention, amelioration or treatment of any disease or condition as described above, e.g., an autoimmune of inflammatory disease or condition.

What is claimed is:

1. A compound of formula I

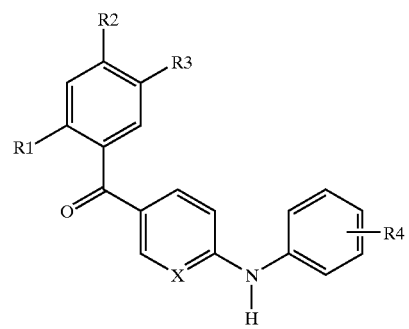

wherein

X is N or CH;

R1 is H, halogen, or optionally substituted (lower alkoxy, lower alkyl or halo-substituted lower alkyl);

R2 is H, or optionally substituted (heterocyclyl, lower alkyl lower alkene, lower alkyne or lower alkoxy);

R3 is H, or optionally substituted (heterocyclyl, lower alkyl lower alkene, lower alkyne or lower alkoxy); or R2 and R3 are linked together to form an optionally substituted 4- to 6-membered heterocyclic ring containing one or more hetero atoms selected from O, S, N, NR, where R is H or lower alkyl, and R4 represents two or three independent halogen substituents, or a pharmaceutically-acceptable and -cleavable ester or acid addition salt thereof.

2. A compound according to claim 1 of Formulae II or III

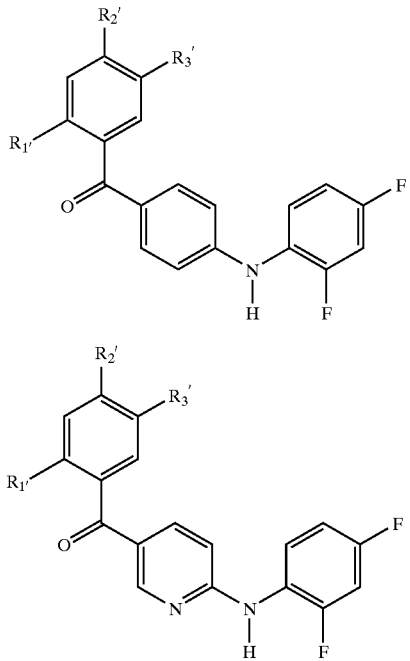

wherein

R1' is halo, $C_1$–$C_4$ lower alkyl, $C_1$–$C_4$ lower alkoxy or halo-substituted $C_1$–$C_4$ lower alkyl;

R2' and R3' are, independently of one another, H or optionally substituted ($C_1$–$C_7$alkenyl, $C_1$–$C_7$alkynyl, $C_5$–$C_7$N-heterocyclyl $C_1$–$C_4$lower alkoxy, $C_5$–$C_7$N-heterocyclyl) wherein the $C_5$–$C_7$N-heterocyclyl optionally contains a further hetero atom, and the optional substitution comprises 1 or 2 substituents, separately selected from $C_{1-4}$alkyl, halogen, hydroxy, $C_{1-4}$alkoxy, optionally mono-or di-N-$C_{1-4}$alkyl substituted amino, or optionally substituted $C_5$–$C_7$N-heterocyclyl, or R2' and R3' are linked to form an imidazole ring optionally substituted by 1 or 2 substituents, separately selected from $C_{1-4}$alkyl, halogen, hydroxy, $C_{1-4}$alkoxy, or optionally mono-or di-N-$C_{1-4}$alkyl substituted amino;

or a pharmaceutically-acceptable and -cleavable ester or acid addition salt thereof.

3. A compound according to claim 1 selected from the following compounds:

(2-Chloro-phenyl)-[4-(2,4-difluoro-phenylamino)-phenyl]-methanone;
[4-(2,4-Difluoro-phenylamino)-phenyl]-(2-methoxy-phenyl)-methanone;
(2-Chloro-5-pyridin-4-yl-phenyl)-[4-(2,4-difluoro-phenylamino)-phenyl]-methanone;
[2-Chloro-4-(2-morpholin-4-yl-ethoxy)-phenyl]-[4-(2,4-difluoro-phenylamino)-phenyl]-methanone;
[5-(3-Amino-3-methyl-but-1-ynyl)-2-methoxy-phenyl]-[4-(2,4-difluoro-phenylamino)-phenyl]-methanone;
[4-(2,4-Difluoro-phenylamino)-phenyl]-[5-(3-dimethylamino-prop-1-ynyl)-2-methoxy-phenyl]-methanone;
[4-(2,4-Difluoro-phenylamino)-phenyl]-[2-methoxy-5-(3-morpholin-4-yl-prop-1-ynyl)-phenyl]-methanone;
[4-(2,4-Difluoro-phenylamino)-phenyl]-{2-methoxy-5-[3-(4-methyl-piperazin-1-yl)-prop-1-ynyl]-phenyl}-methanone;
[4-(2,4-Difluoro-phenylamino)-phenyl]-[2-methoxy-5-((E)-3-morpholin-4-yl-propenyl)-phenyl]-methanone;
[4-(2,4-Difluoro-phenylamino)-phenyl]-[5-((E)-3-dimethylamino-propenyl)-2-methoxy-phenyl]-methanone
[6-(2,4-Difluoro-phenylamino)-pyridin-3-yl]-(2-methoxy-5-pyridin-2-yl-phenyl)-methanone;
[6-(2,4-Difluoro-phenylamino)-pyridin-3-yl]-[2-methoxy-5-(2-piperazin-1-yl-pyrimidin-4-yl)-phenyl]-methanone;
[6-(2,4-Difluoro-phenylamino)-pyridin-3-yl]-[5-(3-dimethylamino-prop-1-ynyl)-2-methoxy-phenyl]-methanone;
[6-(2,4-Difluoro-phenylamino)-pyridin-3-yl]-(2-methoxy-5-pyridin-4-yl-phenyl)-methanone;
[5-(3-Amino-3-methyl-but-1-ynyl)-2-methoxy-phenyl]-[6-(2,4-difluoro-phenylamino)-pyridin-3-yl]-methanone;
(2Chloro-5-pyridin-4-yl-phenyl)-[6-(2,4-difluoro-phenylamino)-pyridin-3-yl]-methanone;
[5-(3-Amino-3-methyl-but-1-ynyl)-2-chloro-phenyl]-[6-(2,4-difluoro-phenylamino)-pyridin-3-yl]-methanone;
(2-Chloro-4-piperazin-1-yl-phenyl)-[6-(2,4-difluoro-phenylamino)-pyridin-3-yl]-methanone;
(6-Chloro-2-methyl-3.H.-benzoimidazol-5-yl)-[6-(2,4-difluoro-phenylamino)-pyridin-3-yl]-methanone;
[6-(2,4-Difluoro-phenylamino)-pyridin-3-yl]-(6-methoxy-2-methyl-3.H.-benzoimidazol-5-yl)-methanone;
[6-(2,4-Difluoro-phenylamino)-pyridin-3-yl]-[2-methoxy-5-(3-morpholin-4-yl-prop-1-ynyl)-phenyl]-methanone;
[6-(2,4-Difluoro-phenylamino)-pyridin-3-yl]-{2-methoxy-5-[3-(4-methyl-piperazin-1-yl)-prop-1-ynyl]-phenyl}-methanone;
[4-(2,4-Difluoro-phenylamino)-phenyl]-[5-(4-hydroxy-1-methyl-piperidin-4-ylethynyl)-2-methoxy-phenyl]-methanone;
[4-(2,4-Difluoro-phenylamino)-phenyl]-{5-[(E)-2-(4-hydroxy-1-methyl-piperidin-4-yl)-vinyl]-2-methoxy-phenyl}-methanone;
[6-(2,4-Difluoro-phenylamino)-pyridin-3-yl]-[5-(1,2-dimethyl-1.H.-imidazol-4-yl)-2-methoxy-phenyl]-methanone;

or a pharmaceutically-acceptable and -cleavable ester or acid addition salt thereof.

4. A method of inhibiting production of soluble TNF or of reducing inflammation in a subject in need of such treatment which method comprises administering to said subject an effective amount of a compound of claim 1 or a pharmaceutically-acceptable and -cleavable ester or acid addition salt thereof.

5. A pharmaceutical composition comprising a compound of claim 1 or a pharmaceutically-acceptable and -cleavable ester or acid addition salt thereof in association with a pharmaceutically acceptable diluent or carrier.

6. A process for the preparation of a compound of formula I as defined in claim 1 which comprises a) amination of a 4-bromobenzophenone of formula IV with 2,4-difluoroaniline;

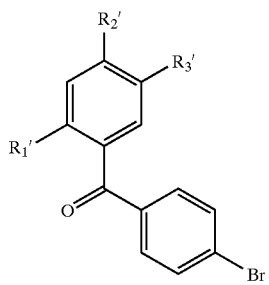

IV where R1' is halo, $C_1$–$C_4$ lower alkyl, $C_1$–$C_4$ lower alkoxy or halo-substituted $C_1$–$C_4$ lower alkyl; R2' and R3' are, independently of one another, H or optionally substituted ($C_1$–$C_7$ alkenyl, $C_1$–$C_7$alkynyl, $C_1$–$C_7$N-heterocyclyl, $C_1$–$C_4$ lower alkoxy, $C_5$–$C_7$N-heterocyclyl) wherein the $C_5$–$C_7$N-heterocyclyl optionally contains a further hetero atom, and the optional substitution comprises 1 or 2 substituents, separately selected from $C_1$–$C_4$ alkyl, halogen, hydroxy, $C_1$–$C_4$alkoxy, optionally mono-or di-N-$C_1$–$C_4$ alkyl substituted amino, or optionally substituted $C_5$–$C_7$N-heterocyclyl, or R2' and R3' are linked to form an imidazole ring optionally substituted by 1 or 2 substituents, separately selected from $C_1$–$C_4$alkyl, halogen, hydroxy, $C_1$–$C_4$alkoxy, or optionally mono-or di-N-$C_1$–$C_4$alkyl substituted amino.

7. A process for the preparation of a compound of formula IIIa

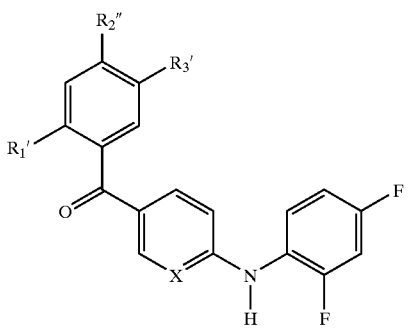

IIIa in which R2" is H, R1' is halo, $C_1$–$C_4$ lower alkyl, $C_1$–$C_4$ lower alkoxy or halo-substituted $C_1$–$C_4$ lower alkyl, R3' is optionally substituted ($C_1$–$C_7$ alkenyl, $C_1$–$C_1$alkenyl, $C_1$–$C_7$N-heterocyclyl, $C_1$–$C_4$ lower alkoxy, $C_5$–$C_7$N-heterocyclyl) wherein the $C_5$–$C_7$N-heterocyclyl optionally contains a further hetero atom, and the optional substitution comprises 1 or 2 substituents, separately selected from $C_1$–$C_4$ alkyl, halogen, hydroxy, $C_1$–$C_4$alkoxy, optionally mono-or di-N-$C_1$–$C_4$ alkyl substituted amino, or optionally substituted $C_5$–$C_7$N-heterocyclyl, and X is N or CH, which process comprises coupling of a bromo derivative of formula VI

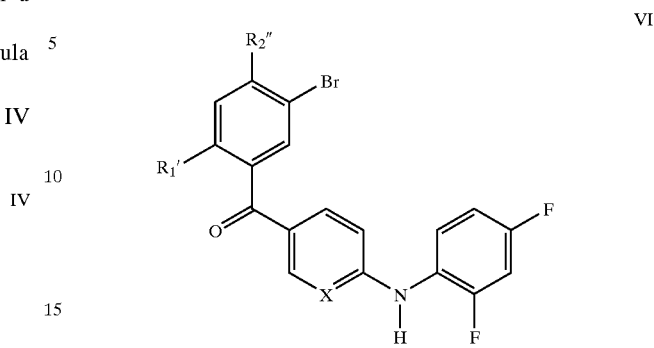

VI wherein, R2" is H, R1' is halo, $C_1$–$C_4$ lower alkyl, $C_1$–$C_4$ lower alkoxy or halo-substituted $C_1$–$C_4$ lower alkyl, R3' is optionally substituted ($C_1$–$C_7$alkenyl, $C_1$–$C_7$alkynyl, $C_1$–$C_7$N-heterocyclyl, $C_1$–$C_4$ lower alkoxy, $C_5$–$C_7$N-heterocyclyl) wherein the $C_5$–$C_7$N-heterocyclyl optionally contains a further hetero atom, and the optional substitution comprises 1 or 2 substituents, separately selected from $C_1$–$C_4$ alkyl, halogen, hydroxy, $C_1$–$C_4$alkoxy, optionally mono-or di-N-$C_1$–$C_4$ alkyl substituted amino, or optionally substituted $C_5$–$C_7$N-heterocyclyl, and X is N or CH, with a trialkyl tin heteroaryl compound when R3' is heteroaryl or with a lower alkynyl or alkenyl compound when R3' is a lower alkynyl or alkenyl substituent.

8. A process for the preparation of a compound of formula IX

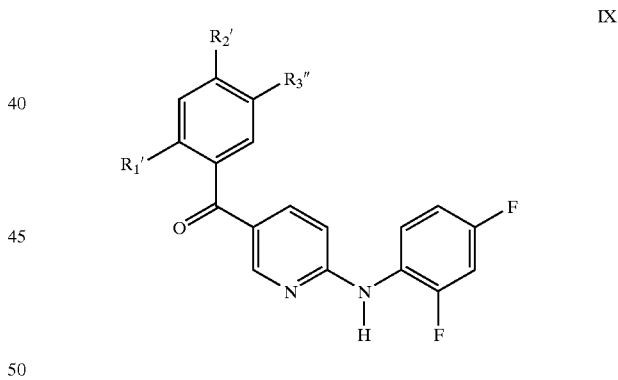

IX where R1' is halo, $C_1$–$C_4$ lower alkyl, $C_1$–$C_4$ lower alkoxy or halo-substituted $C_1$–$C_4$ lower alkyl; R2' is H or optionally substituted ($C_1$–$C_7$ alkenyl, $C_1$–$C_7$alkynyl, $C_1$–$C_7$N-heterocyclyl, $C_1$–$C_4$ lower alkoxy, $C_5$–$C_7$N-heterocyclyl) wherein the $C_5$–$C_7$N-heterocyclyl optionally contains a further hetero atom, and the optional substitution comprises 1 or 2 substituents, separately selected from $C_1$–$C_4$ alkyl, halogen, hydroxy, $C_1$–$C_4$alkoxy, optionally mono-or di-N-$C_1$–$C_4$ alkyl substituted amino, or optionally substituted $C_5$–$C_7$N-heterocyclyl and R3" is H or R2' and R3" are linked together to form an optionally substituted 4- to 6-membered heterocyclic ring containing one or more hetero atoms selected from O, S, N, NR, where R is H or lower alkyl which process comprises oxidation of the corresponding alcohol of formula X

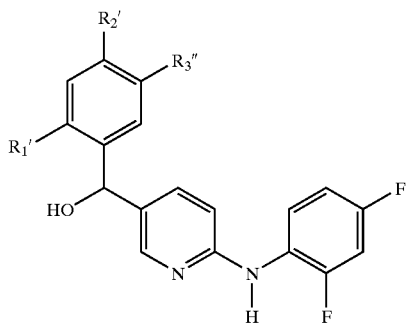

where R1' is halo, $C_1$–$C_4$ lower alkyl, $C_1$–$C_4$ lower alkoxy or halo-substituted $C_1$–$C_4$ lower alkyl; R2' is H or optionally substituted ($C_1$–$C_7$ alkenyl, $C_1$–$C_7$ alkynyl, $C_1$–$C_7$N-heterocyclyl, $C_1$–$C_4$ lower alkoxy, $C_5$–$C_7$N-heterocyclyl) wherein the $C_5$–$C_7$N-heterocyclyl optionally contains a further hetero atom, and the optional substitution comprises 1 or 2 substituents, separately selected from $C_1$–$C_4$ alkyl, halogen, hydroxy, $C_1$–$C_4$ alkoxy, optionally mono-or di-N-$C_1$–$C_4$ alkyl substituted amino, or optionally substituted $C_5$–$C_7$N-heterocyclyl and R3" is H or R2' and R3" are linked together to form an optionally substituted 4- to 6-membered heterocyclic ring containing one or more hetero atoms selected from O, S, N, NR, where R is H or lower alkyl.

9. The pharmaceutical composition of claim 5 which composition has immunosuppressant or anti-inflammatory properties.

* * * * *

UNITED STATES PATENT AND TRADEMARK OFFICE
CERTIFICATE OF CORRECTION

PATENT NO.    : 6,919,336 B2
DATED         : July 19, 2005
INVENTOR(S)   : Laszlo Revesz It is certified that error appears in the above-identified patent and that said Letters Patent is hereby corrected as shown below:

Title page,
Item [54], Title, should read -- HALOGENATED AMINOBENZOPHENONES AND AMINOBENZOYLPYRIDINES AS INHIBITORS OF IL-1 AND TNF --.

Signed and Sealed this

Fourth Day of October, 2005

JON W. DUDAS
*Director of the United States Patent and Trademark Office*